US008889874B2

(12) United States Patent
Ahmed et al.

(10) Patent No.: US 8,889,874 B2
(45) Date of Patent: Nov. 18, 2014

(54) IMIDAZOLONE-CHALCONE DERIVATIVES AS POTENTIAL ANTICANCER AGENT AND PROCESS FOR THE PREPARATION THEREOF

(75) Inventors: Kamal Ahmed, Hyderabad (IN); Ramakrishna Gadupudi, Hyderabad (IN); Balakishan Gorre, Hyderabad (IN); Raju Paidakula, Hyderabad (IN); Viswanath Arutla, Hyderabad (IN); Balakrishna Moku, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/514,697

(22) PCT Filed: Dec. 14, 2010

(86) PCT No.: PCT/IB2010/003224
§ 371 (c)(1),
(2), (4) Date: Jul. 10, 2012

(87) PCT Pub. No.: WO2011/086412
PCT Pub. Date: Jul. 21, 2011

(65) Prior Publication Data
US 2013/0066081 A1 Mar. 14, 2013

(30) Foreign Application Priority Data
Jan. 12, 2010 (IN) ................ 68/DEL/2010

(51) Int. Cl.
*C07D 233/70* (2006.01)
*C07D 401/04* (2006.01)
*A61K 31/44* (2006.01)
*C07D 405/04* (2006.01)
*C07D 409/04* (2006.01)

(52) U.S. Cl.
CPC ............ *C07D 401/04* (2013.01); *C07D 233/70* (2013.01); *C07D 405/04* (2013.01); *C07D 409/04* (2013.01)
USPC .................. 546/274.1; 548/315.1; 548/315.7; 548/325.5

(58) Field of Classification Search
None
See application file for complete search history.

(56) References Cited

U.S. PATENT DOCUMENTS

2004/0048858 A1 3/2004 Sikorski et al.

FOREIGN PATENT DOCUMENTS

WO 01/46110 A2 6/2001
WO 2004/035525 A1 4/2004

OTHER PUBLICATIONS

Edwards, et al., "Chalcones: A New Class of Antimitotic Agents," Journal of Medicinal Chemistry, vol. 33, No. 7, pp. 1948-1954 (1990).
Kamal, et al., "Synthesis and Anti-cancer Activity of Chalcone Linked Imidazolones," Bioorganic & Medicinal Chemistry Letters, vol. 20, No. 16, pp. 4865-4869 (2010).
Pettit et al., "Isolation and Structure of the Strong Cell Growth and Tubulin Inhibitor Combretastatin A-4," Experientia, vol. 45, pp. 209-211 (1989).
Ohsumi et al., "Syntheses and Antitumor Activity of Cis-Restricted Combretastatins: 5-Membered Heterocyclic Analogues," Bioorganic & Medicinal Chemistry Letters, vol. 8, pp. 3153-3158 (1998).
Wu-Wong et al., "Identification and Characterization of A-105972, an Antineoplastic Agent,", Cancer Research, vol. 61, pp. 1486-1492 (2001).

(Continued)

*Primary Examiner* — Zinna Northington Davis
(74) *Attorney, Agent, or Firm* — McDermott Will & Emery LLP

(57) ABSTRACT

The present invention provides Chalcone linked Imidazolone compounds of formula A as anti cancer agent against fifty three human cancer cell lines.

Formula A

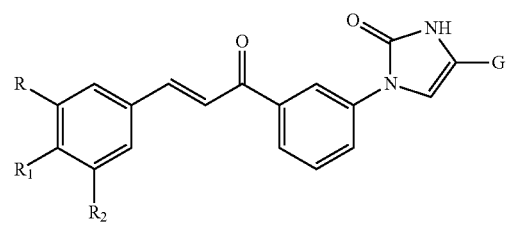

wherein

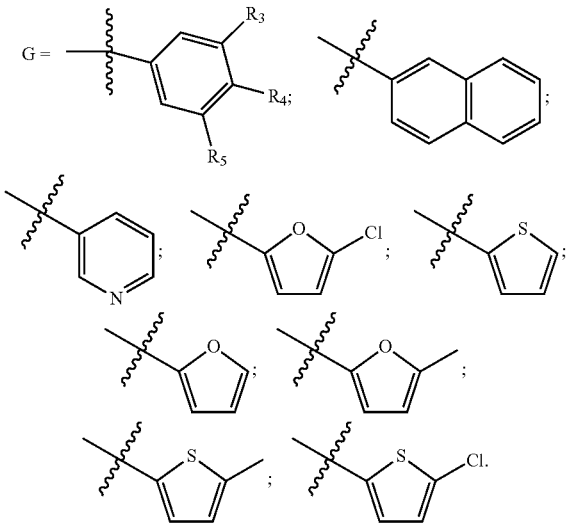

R = H, OMe
$R_1$ = H, Cl, F, OH, OMe
$R_2$ = H, OH, OMe
$R_3$ = H, OMe, $CH_3$
$R_4$ = H, Cl, F, OH, OMe, $CH_3$
$R_5$ = H, OMe, $CH_3$

14 Claims, 2 Drawing Sheets

(56) References Cited

OTHER PUBLICATIONS

Congiu et al., "Design, Synthesis, and in Vitro Antitumor Activity of New 1,4-diarylimidazole-2-ones and their 2-thione Analogues," Bioorganic & Medicinal Chemistry Letters, vol. 18, pp. 989-993 (2008).

Park et al., "Licochalcone A: An Inducer of Cell Differentiation and Cytotoxic Agent from Pogostemon cablin," Planta Medica, vol. 64, pp. 464-466 (1998).

De Vincenzo et al., "Effect of Synthetic and Naturally Occurring Chalcones on Ovarian Cancer Cell Growth: Structure-Activity Relationships," Anti-Cancer Drug Design, vol. 10, No. 6, pp. 481-490 (1995).

Rui, "Research and Development of Cancer Chemopreventive Agents in China," Journal of Cellular Biochemistry Supplement, vol. 27, pp. 7-11 (1997).

Satomi, "Inhibitory Effects of 3'-Methyl-3-Hydroxy-Chalcone on Proliferation of Human Malignant Tumor Cells and on Skin Carcinogenesis," International Journal of Cancer, vol. 55, pp. 506-514 (1993).

Calliste et al., "Chalcones Structural Requirements for Antioxidant, Estrogenic and Antiproliferative Activities," Anticancer Research, vol. 21, pp. 3949-3956 (2001).

International Search Report from PCT/IB2010/003224 dated Jul. 25, 2011.

Scheme-1

IMIDAZOLONE-CHALCONE DERIVATIVES AS POTENTIAL ANTICANCER AGENT AND PROCESS FOR THE PREPARATION THEREOF

CROSS REFERENCE TO PRIOR APPLICATIONS

This application is a U.S. National Phase Application under 35 U.S.C. §371 of International Application No. PCT/IB2010/003224, filed on Dec. 14, 2010 and claims benefit of priority to Indian Patent Application No. 68/DEL/2010, filed on Jan. 12, 2010. The International Application was published on Jul. 21, 2011 as WO 2011/086412 A2 under PCT Article 21(2). All of these applications are incorporated herein by reference.

FIELD OF THE INVENTION

The present invention relates to chalcone linked imidazolone compounds of formula A as potential anti cancer agents and a process for the preparation thereof.

Formula A

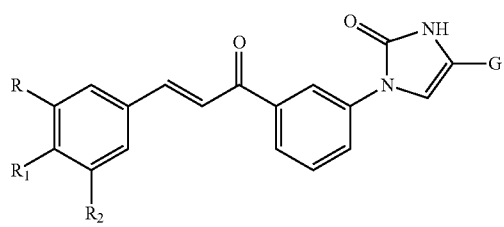

wherein

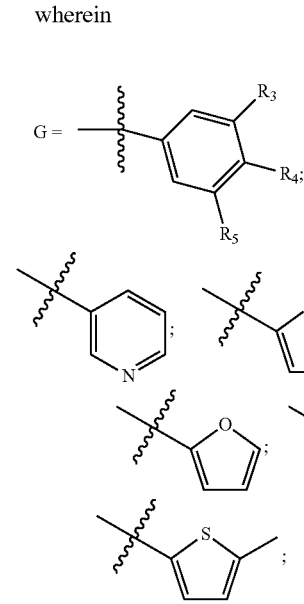

R = H, OMe
$R_1$ = H, Cl, F, OH, OMe
$R_2$ = H, OH, OMe
$R_3$ = H, OMe, $CH_3$
$R_4$ = H, Cl, F, OH, OMe, $CH_3$
$R_5$ = H, OMe, $CH_3$

The structural formula of the representative group of Chalcone linked imidazolone compounds are given below:

Formula 3a-j to 11a-j

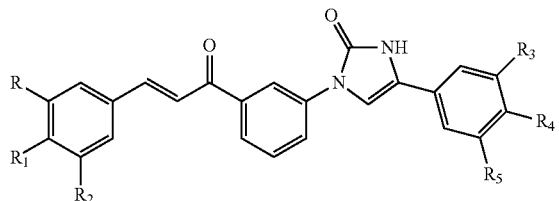

R = H, OMe
$R_1$ = H, Cl, F, OH, OMe
$R_2$ = H, OH, OMe
$R_3$ = H, OMe, $CH_3$
$R_4$ = H, Cl, F, OH, OMe, $CH_3$
$R_5$ = H, OMe, $CH_3$

Formula 12a-i

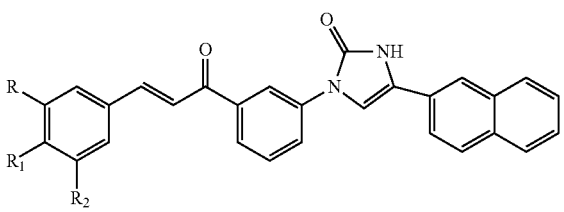

R = H, OMe
$R_1$ = H, Cl, F, OH, OMe
$R_2$ = H, OH, OMe

Formula 13a-i

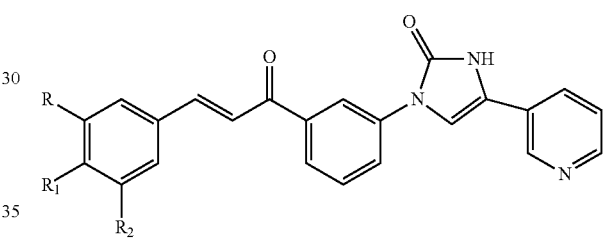

R = H, OMe
$R_1$ = H, Cl, F, OH, OMe
$R_2$ = H, OH, OMe

Formula 14a-i to 19a-i

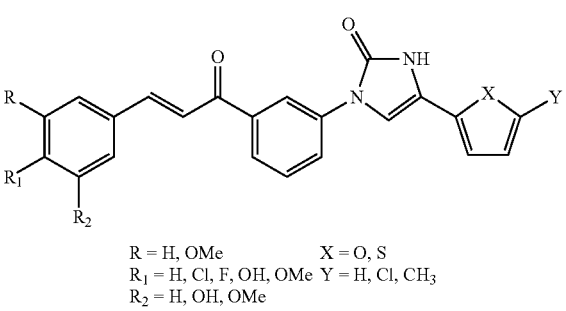

R = H, OMe
$R_1$ = H, Cl, F, OH, OMe
$R_2$ = H, OH, OMe
X = O, S
Y = H, Cl, $CH_3$

BACKGROUND OF THE INVENTION

References may be made to Journal "Pettit, G. R.; Singh, S. B.; Hamel, E.; Lin, C. M.; Alberts, D. S.; Garcia Kendall, D. *Experientia* 1989, 45, 209" wherein Combretastatins, a group of antimitotic agents isolated from the bark of the South African willow tree *Combretum caffrum* Kuntz has attracted considerable interest of medicinal chemists in the design of analogues as novel antitumor agents. Combretastatin A-4 (1) appears to be the most active in the group, and remarkably simple in the chemical structure, while possessing unique dual features anti-tubulin and anti-vascular agent. CA-4 strongly inhibits the polymerization of tubulin by binding to the colchicine site. Because of its simple structure, a large number of CA-4 analogues have been developed and evaluated in SAR studies. Among synthetic small-molecule tubulin inhibitors, replacement of the double bond of with a carbonyl group furnished a benzophenonetype CA-4 analogue named phenstatin. This compound demonstrated interesting efficacy in a variety of tumor models while retaining the characteristics of (1) The 2-aminobenzophenone derivative also strongly inhibited cancer cell growth and tubulin polymerization and caused mitotic arrest, as phenstatin did.

Reference may be made to Journal "Ohsumi, K; Hatanaka, T.; Fujita, K.; Nakagawa, R.; Fukuda, Y.; Nihei, Y.; Suga, Y.; Morinaga, Y.; Akiyama, Y.; Tsuji, T. Bioorg. Med. Chem. Lett. 1998, 8, 3153" wherein many synthetic analogues have been developed following the strategy of design of two-atom bridgehead analogues utilizing 1,2-oriented heterocycles are described. In contrast, a limited number of analogues have been successfully designed following the strategy of three-atom bridgeheads 1,3-oriented with a linear- or heterocycle-linker inserted between the two aryl rings of combretastatins.

Reference may be made to Journal "Edwards, M. L.; Stemerick, D. M.; Sunkara, P. S. J. Med. Chem. 1990, 33, 1948A" wherein a series of chalcones and a large collection of oxazoline and oxadiazoline derivatives are described.

Reference may be made to Journal "Wu-Wong, J. R.; Alder, J. D.; Alder, L.; Burns, D. J.; Han, E. K.; Credo, B.; Tahir, S. K.; Dayton, B. D.; Ewing, P. J.; Chiou, W. J. Cancer Res. 2001, 61, 1486" wherein analogues of A-105972 obtained in the Abbott Laboratories. modifications of the ethylene bridge in this class of compounds with the five member ring like imidazolone type of compounds (4) have led to interesting biological profile, particularly exhibits significant anticancer activity "Cenzo Congiu, Maria Teresa Cocco, Valentina Onnis, Bioorg. Med. Chem. Lett. 2008, 18, 989"

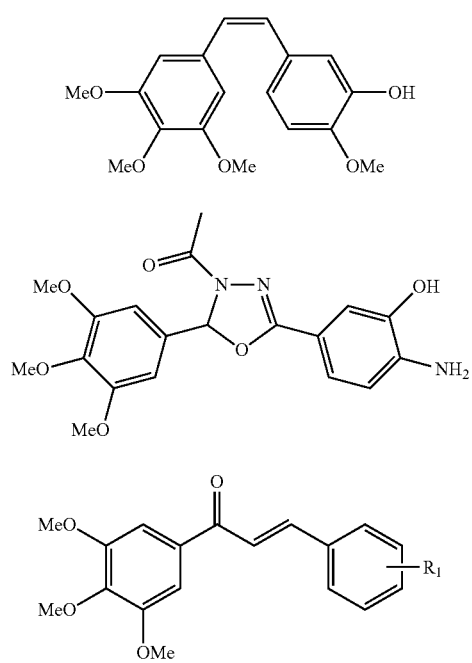

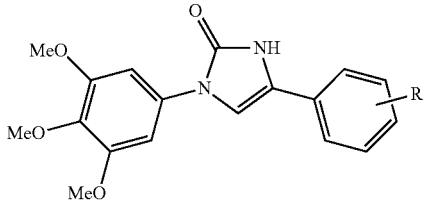

Chemical Structures of Combretstatin (1), A-105972 (2), Chalcones (3), and Imidazolones (4)

Furthermore Chalcones (3) are a class of anticancer agents that have shown promising therapeutic efficacy for the management of human cancers. Chalcones, considered as the precursor of flavonoids and isoflavonoids, are abundant in edible plants.

Chemically they consist of open-chain flavonoids in which the two aromatic rings are joined by a three-carbon R,â-unsaturated carbonyl system. Licochalcone-A, a chalcone derivative found in the licorice root, has been associated with a wide variety of anticancer effects "Park, E. J.; Park, H. R.; Lee, J. S.; Kim, J. Planta Med. 1998, 64, 464" Chalcones inhibit the proliferation of both established and primary ovarian cancer cells "De Vincenzo, R.; Scambia, G.; Benedetti Panici, P.; Ranelletti, F. O.; Bonanno, G.; Ercoli, A.; Delle Monache, F.; Ferrari, F.; Piantelli, M.; Mancuso, S. Anticancer Drug Des. 1995, 10, 481". In vivo, chalcones have been demonstrated to be effective as antitumor agents in skin carcinogenesis "Statomi, Y. Int. J. Cancer 1993, 55, 506) and chemopreventive agents in several experimental models (Rui, H. J. Cell. Biochem. 1997, 67, 7". Recent studies have shown that these chalcones induce apoptosis in variety of cell types, including breast cancers "Claude-Alain, C.; Jean-Chritophe, L.; Patrick, T.; Christelle, P.; Gerard, H.; Albert-Jose, C.; Jean-Luc, D. Anticancer Res. 2001, 21, 3949"

References may be made to an Journal "Cenzo congiu, Maria Teresa Cocco and vValentina onnis, Bioorganic and medicinal chemistry letters, 18, 2008, 989-993" wherein a series of new 1,4-diarylimidazol-2(3H)-one derivatives and their 2-thione analogues has been prepared and evaluated in vitro for antitumor activity against the NCI human cancer cell panel. Compounds bearing a 3,4,5-trimethoxyphenyl ring linked to either N-1 or C-4 position of the imidazole core demonstrated an interesting profile of cytotoxicity with preferential activity against leukemic cell lines. Compound 13 exhibited a potent antitumor activity against MOLT-4 (GI50=20 nM) and SR (GI50=32 nM) cell lines.

References may be made to an article published in bioorganic and medical chemistry letters 18 (2008) 989-993 "Design, synthesis, and in vitro antitumor activity of new 1,4-diarylimidazole-2-ones and their 2-thione analogues" wherein a series of new 1,4-diarylimidazol-2(3H)-one derivatives and their 2-thione analogues has been prepared and evaluated in vitro for antitumor activity against the NCI human cancer cell panel. Compounds bearing a 3,4,5-trimethoxyphenyl ring linked to either N-1 or C-4 position of the imidazole core demonstrated an interesting profile of cytotoxicity with preferential activity against leukemia cell lines.

Present invention provides improved anticancer activity against fifty three human cancer cell lines.

OBJECTIVES OF THE INVENTION

The main objective of the present invention is to provide chalcone linked imidazolone compounds of general formula A as anti cancer agent.

Another objective of the present invention is to provide process for the preparation of chalcone linked imidazolone compounds of general formula A.

SUMMARY OF THE INVENTION

Accordingly, the present invention provides chalcone linked imidazolone compounds of formula A Formula A wherein

G = as anticancer agent and the structural formula of the representative group of Chalcone linked imidazolones are:

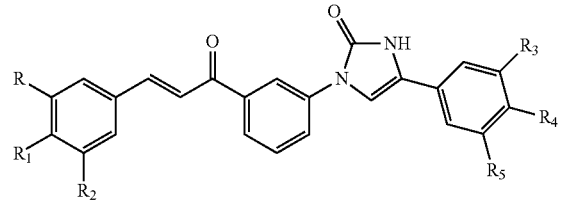

Formula 3a-j to 11a-j

R = H, OMe          $R_3$ = H, OMe, $CH_3$
$R_1$ = H, Cl, F, OH, OMe   $R_4$ = H, Cl, F, OH, OMe, $CH_3$
$R_2$ = H, OH, OMe       $R_5$ = H, OMe, $CH_3$

Formula 12a-i

R = H, OMe
$R_1$ = H, Cl, F, OH, OMe
$R_2$ = H, OH, OMe

Formula 13a-i

R = H, OMe
$R_1$ = H, Cl, F, OH, OMe
$R_2$ = H, OH, OMe

Formula 14a-i to 19a-i

R = H, OMe          X = O, S
$R_1$ = H, Cl, F, OH, OMe   Y = H, Cl, $CH_3$
$R_2$ = H, OH, OMe

In an embodiment of the present invention, the invention provides chalcone linked imidazolone compounds of formula 3a, 3b, 3f, 4a, 4f, 5a, 5b, 5d, 5f and 12b exhibits an in vitro anticancer activity against the standard fifty three human cancer cell lines, derived from nine cancer types leukemia cell line, non small cell lung cell line, colon cell line, CNS cell line, renal cell line, prostate cell line, ovarian cell line, breast and melanoma cell line.

In yet another embodiment of the present invention, the concentration of the chalcone linked imidazolone compounds of formula 3a, 3b, 3f, 4a, 4f, 5a, 5b, 5d, 5f and 12b used for in vitro anticancer activity against two leukemia cancer cell line (RPMI-8226 and K-562) for $GI_{50}$ are in the range of 1.67 to 2.04, 1.35 to 2.35, 1.33 to 1.42, 2.115 to 3.35, 0.40 to 1.55, 0.50 to 0.62, 0.92 to 1.27, 0.23 to 0.59, 3.69 to 3.92 and 1.43 to 1.67 µm respectively at an exposure period of at least 48 hrs.

In yet another embodiment of the present invention, the concentration of the chalcone linked imidazolone compounds of formula 3a, 3b, 3f, 4a, 4f, 5a, 5b, 5d, 5f and 12b as anti-cancer agent exhibiting an in vitro anticancer activity against nine Non-small cell lung cancer cell line (A549/ATCC, EKVX, HOP-62, HOP-92, NCI-H226, NCI-H23, NCI-H322M, NCI-H460 and NCI-H522) for $GI_{50}$ are in the range of 1.48 to 3.90, 2.85 to 13.4, 1.26 to 9.61, 2.49 to 24.8, 1.60 to 3.55, 0.95 to 14.6, 1.56 to 35.2, 1.05 to 14.4, 3.56 to 85.2 and 0.51 to 3.38 µm respectively at an exposure period of at least 48 hrs.

In yet another embodiment of the present invention, the concentration of the chalcone linked imidazolone compounds of formula 3a, 3b, 3f, 4a, 4f, 5a, 5b, 5d, 5f and 12b as anti-cancer agent exhibiting an in vitro anticancer activity against seven colon cancer cell line (COLO 205, HCC-2998, HCT-116, HCT-15, HT29, KM12 and SW-620) for $GI_{50}$ are in the range of 1.40 to 3.77, 1.77 to 6.61, 1.46 to 3.40, 1.83 to 4.09, 1.23 to 13.7, 0.33 to 1.51, 0.37 to 1.84, 0.74 to 1.92, 1.39 to 7.38 and 0.22 to 2.13 µm respectively at an exposure period of at least 48 hrs.

In yet another embodiment of the present invention, the concentration of the chalcone linked imidazolone compounds of formula 3a, 3b, 3f, 4a, 4f, 5a, 5b, 5d, 5f and 12b as anti-cancer agent exhibiting an in vitro anticancer activity against six CNS cancer cell line (SF-268, SF-295, SF-539, SNB-19, SNB-75 and U251) for $GI_{50}$ are in the range of 1.91 to 3.90, 2.25 to 13.9, 1.78 to 10.5, 1.61 to 18.2, 0.58 to 1.92, 0.63 to 4.47, 0.88 to 4.95, 1.23 to 4.96, 2.12 to 24.3 and 1.09 to 1.88 µm respectively at an exposure period of at least 48 hrs.

In yet another embodiment of the present invention, the concentration of the chalcone linked imidazolone compounds of formula 3a, 3b, 3f, 4f, 5a, 5b, 5d, 5f and 12b as anticancer agent exhibiting an in vitro anticancer activity against eight renal cancer cell line (A498, 786-0, ACHN, CAKI-1, RXF 393, SN12C, TK-10 and UO-31) for $GI_{50}$ are in the range of 1.35 to 5.29, 3.40 to 6.08, 1.67 to 6.40, 1.89 to 14.3, 0.55 to 3.71, 1.38 to 3.02, 1.61 to 3.50, 0.96 to 20.3, 2.14 to 30.2 and 1.26 to 3.45 µm respectively at an exposure period of at least 48 hrs.

In yet another embodiment of the present invention, the concentration of the chalcone linked imidazolone compounds of formula 3a, 3b, 3f, 4a, 5a, 5b, 5d and 12b as anticancer agent exhibiting an in vitro anticancer activity against one prostate cancer cell line (PC-3) for $GI_{50}$ are 2.52, 3.05, 1.95, 2.82, 3.26, 6.22, 2.63, 16.5 and 1.85 µm respectively at an exposure period of at least 48 hrs.

In yet another embodiment of the present invention, the concentration of the chalcone linked imidazolone compounds of formula 3a, 3b, 3f, 4a, 4f, 5a, 5b, 5d, 5f and 12b as anti-cancer agent exhibiting an in vitro anticancer activity against six ovarian cancer cell line (OVCAR-3, OVCAR-4, OVCAR-5, OVCAR-8, NCI/ADR-RES and SK-OV-3) for $GI_{50}$ are in the range of 2.04 to 5.19, 2.56 to 6.08, 1.56 to 4.64, 2.80 to 11.1, 0.99 to 4.21, 1.10 to 3.27, 1.70 to 4.60, 1.48 to 5.12, 2.36 to 31.4 and 1.33 to 2.33 µm respectively at an exposure period of at least 48 hrs.

In yet another embodiment of the present invention, the concentration of the chalcone linked imidazolone compounds of formula 3a, 3b, 3f, 4a, 4f, 5a, 5b, 5d, 5f and 12b as anti-cancer agent exhibiting an in vitro anticancer activity against five breast cancer cell line (MCF7, MDA-MB-231/ATCC, HS 578T, 8T-549 and TD-47D) for $GI_{50}$ are in the range of 1.55 to 4.16, 3.18 to 5.25, 2.30 to 4.67, 2.47 to 9.32, 1.29 to 4.00, 0.31 to 3.41, 0.44 to 5.48, 0.47 to 4.19, 1.74 to 13.8 and 0.47 to 2.01 µm respectively at an exposure period of at least 48 hrs.

In yet another embodiment of the present invention, the concentration of the chalcone linked imidazolone compounds of formula 3a, 3b, 3f, 4a, 4f, 5a, 5b, 5d, 5f and 12b as anti-cancer agent exhibiting an in vitro anticancer activity against (LOX IMVI, MALME-3M, M14, MDA-MB-435, SK-MEL-2, SK-MEL-28, SK-MEL-5, UACC-257 and UACC-62) melanoma cancer cell line for $GI_{50}$ are in the range of 1.59 to 6.81, 2.03 to 13.3, 1.63 to 8.69, 1.85 to 8.26, 1.53 to 4.07, 0.48 to 2.06, 0.72 to 3.04, 1.23 to 3.02, 1.72 to 18.1 and 0.85 to 4.13 µm respectively at an exposure period of at least 48 hrs.

In yet another embodiment of the present invention, chalcone linked imidazolone compounds are represented by:

(3a) 1-3-[(E)-3-(4-hydroxy-3-methoxyphenyl)-2-propenoyl]phenyl-4-phenyl-2,3-dihydro-1H-2-imidazolone (3b) 1-3-[(E)-3-(4-hydroxy-3-methoxyphenyl)-2-propenoyl]phenyl-4-(4-methoxyphenyl)-2,3-dihydro-1H-2-imidazolone (3c) 4-(3,4-dimethoxyphenyl)-1-3-[(E)-3-(4-hydroxy-3-methoxyphenyl)-2-propenoyl]phenyl-2,3-dihydro-1H-2-imidazolone (3d) 1-3-[(E)-3-(4-hydroxy-3-methoxyphenyl)-2-propenoyl]phenyl-4-(3,4,5-trimethoxyphenyl)-2,3-dihydro-1H-2-imidazolone (3e) 4-(4-fluorophenyl)-1-3-[(E)-3-(4-hydroxy-3-methoxyphenyl)-2-propenoyl]phenyl-2,3-dihydro-1H-2-imidazolone (3f) 4-(4-chlorophenyl)-1-3-[(E)-3-(4-hydroxy-3-methoxyphenyl)-2-propenoyl]phenyl-2,3-dihydro-1H-2-imidazolone (3g) 1-3-[(E)-3-(4-hydroxy-3-methoxyphenyl)-2-propenoyl]phenyl-4-(4-methylphenyl)-2,3-dihydro-1H-2-imidazolone (3h) 4-(3,4-dimethylphenyl)-1-3-[(E)-3-(4-hydroxy-3-methoxyphenyl)-2-propenoyl]phenyl-2,3-dihydro-1H-2-imidazolone (3i) 1-3-[(E)-3-(4-hydroxy-3-methoxyphenyl)-2-propenoyl]phenyl-4-(3,4,5-trimethylphenyl)-2,3-dihydro-1H-2-imidazolone (3j) 1-3-[(E)-3-(4-hydroxy-3-methoxyphenyl)-2-propenoyl]phenyl-4-(4-hydroxyphenyl)-2,3-dihydro-1H-2-imidazolone (4a) 1-3-[(E)-3-(3-hydroxyphenyl)-2-propenoyl]phenyl-4-phenyl-2,3-dihydro-1H-2-imidazolone (4b) 1-3-[(E)-3-(3-hydroxyphenyl)-2-propenoyl]phenyl-4-(4-methoxyphenyl)-2,3-dihydro-1H-2-imidazolone (4c) 4-(3,4-dimethoxyphenyl)-1-3-[(E)-3-(3-hydroxyphenyl)-2-propenoyl]phenyl-2,3-dihydro-1H-2-imidazolone (4d) 1-3-[(E)-3-(3-hydroxyphenyl)-2-propenoyl]phenyl-4-(3,4,5-trimethoxyphenyl)-2,3-dihydro-1H-2-imidazolone (4e) 4-(4-fluorophenyl)-1-3-[(E)-3-(3-hydroxyphenyl)-2-propenoyl]phenyl-2,3-dihydro-1H-2-imidazolone (4f) 4-(4-chlorophenyl)-1-3-[(E)-3-(3-hydroxyphenyl)-2-propenoyl]phenyl-2,3-dihydro-1H-2-imidazolone (4g) 1-3-[(E)-3-(3-hydroxyphenyl)-2-propenoyl]phenyl-4-(4-methyl phenyl)-2,3-dihydro-1H-2-imidazolone (4h) 4-(3,4-dimethylphenyl)-1-3-[(E)-3-(3-hydroxyphenyl)-2-propenoyl]phenyl-2,3-dihydro-1H-2-imidazolone (4i) 1-3-[(E)-3-(3-hydroxyphenyl)-2-propenoyl]phenyl-4-(3,4,5-trimethylphenyl)-2,3-dihydro-1H-2-imidazolone (4j) 4-(4-hydroxyphenyl)-1-3-[(E)-3-(3-hydroxyphenyl)-2-propenoyl]phenyl-2,3-dihydro-1H-2-imidazolone (5a) 4-phenyl-1-3-[(E)-3-(3,4,5-trimethoxyphenyl)-2-propenoyl]phenyl-2,3-dihydro-1H-2-imidazolone (5b) 4-(4-methoxyphenyl)-1-3-[(E)-3-(3,4,5-trimethoxyphenyl)-2-propenoyl]phenyl-2,3-dihydro-1H-2-imidazolone
(5c) 4-(3,4-dimethoxyphenyl)-1-3-[(E)-3-(3,4,5-trimethoxyphenyl)-2-propenoyl]phenyl-2,3-dihydro-1H-2-imidazolone
(5d) 4-(3,4,5-trimethoxyphenyl)-1-3-[(E)-3-(3,4,5-trimethoxyphenyl)-2-propenoyl]phenyl-2,3-dihydro-1H-2-imidazolone
(5e) 4-(4-fluorophenyl)-1-3-[(E)-3-(3,4,5-trimethoxyphenyl)-2-propenoyl]phenyl-2,3-dihydro-1H-2-imidazolone
(5f) 4-(4-chlorophenyl)-1-3-[(E)-3-(3,4,5-trimethoxyphenyl)-2-propenoyl]phenyl-2,3-dihydro-1H-2-imidazolone
(5g) 4-(4-methylphenyl)-1-3-[(E)-3-(3,4,5-trimethoxyphenyl)-2-propenoyl]phenyl-2,3-dihydro-1H-2-imidazolone
(5h) 4-(3,4-dimethylphenyl)-1-3-[(E)-3-(3,4,5-trimethoxyphenyl)-2-propenoyl]phenyl-2,3-dihydro-1H-2-imidazolone
(5i) 1-3-[(E)-3-(3,4,5-trimethoxyphenyl)-2-propenoyl]phenyl-4-(3,4,5-trimethylphenyl)-2,3-dihydro-1H-2-imidazolone
(5j) 4-(4-hydroxyphenyl)-1-3-[(E)-3-(3,4,5-trimethoxyphenyl)-2-propenoyl]phenyl-2,3-dihydro-1H-2-imidazolone
(6a) 1-3-[(E)-3-(3,4-dimethoxyphenyl)-2-propenoyl]phenyl-4-phenyl-2,3-dihydro-1H-2-imidazolone
(6b) 1-3-[(E)-3-(3,4-dimethoxyphenyl)-2-propenoyl]phenyl-4-(4-methoxyphenyl)-2,3-dihydro-1H-2-imidazolone
(6c) 4-(3,4-dimethoxyphenyl)-1-3-[(E)-3-(3,4-dimethoxyphenyl)-2-propenoyl]phenyl-2,3-dihydro-1H-2-imidazolone
(6d) 1-3-[(E)-3-(3,4-dimethoxyphenyl)-2-propenoyl]phenyl-4-(3,4,5-trimethoxyphenyl)-2,3-dihydro-1H-2-imidazolone
(6e) 1-3-[(E)-3-(3,4-dimethoxyphenyl)-2-propenoyl]phenyl-4-(4-fluorophenyl)-2,3-dihydro-1H-2-imidazolone
(6f) 4-(4-chlorophenyl)-1-3-[(E)-3-(3,4-dimethoxyphenyl)-2-propenoyl]phenyl-2,3-dihydro-1H-2-imidazolone
(6g) 1-3-[(E)-3-(3,4-dimethoxyphenyl)-2-propenoyl]phenyl-4-(4-methylphenyl)-2,3-dihydro-1H-2-imidazolone
(6h) 1-3-[(E)-3-(3,4-dimethoxyphenyl)-2-propenoyl]phenyl-4-(3,4-dimethylphenyl)-2,3-dihydro-1H-2-imidazolone
(6i) 1-3-[(E)-3-(3,4-dimethoxyphenyl)-2-propenoyl]phenyl-4-(3,4,5-trimethylphenyl)-2,3-dihydro-1H-2-imidazolone
(6j) 1-3-[(E)-3-(3,4-dimethoxyphenyl)-2-propenoyl]phenyl-4-(4-hydroxyphenyl)-2,3-dihydro-1H-2-imidazolone
(7a) 1-3-[(E)-3-(4-methoxyphenyl)-2-propenoyl]phenyl-4-phenyl-2,3-dihydro-1H-2-imidazolone
(7b) 4-(4-methoxyphenyl)-1-3-[(E)-3-(4-methoxyphenyl)-2-propenoyl]phenyl-2,3-dihydro-1H-2-imidazolone
(7c) 4-(3,4-dimethoxyphenyl)-1-3-[(E)-3-(4-methoxyphenyl)-2-propenoyl]phenyl-2,3-dihydro-1H-2-imidazolone
(7d) 1-3-[(E)-3-(4-methoxyphenyl)-2-propenoyl]phenyl-4-(3,4,5-trimethoxyphenyl)-2,3-dihydro-1H-2-imidazolone
(7e) 4-(4-fluorophenyl)-1-3-[(E)-3-(4-methoxyphenyl)-2-propenoyl]phenyl-2,3-dihydro-1H-2-imidazolone
(7f) 4-(4-chlorophenyl)-1-3-[(E)-3-(4-methoxyphenyl)-2-propenoyl]phenyl-2,3-dihydro-1H-2-imidazolone
(7g) 1-3-[(E)-3-(4-methoxyphenyl)-2-propenoyl]phenyl-4-(4-methylphenyl)-2,3-dihydro-1H-2-imidazolone
(7h) 4-(3,4-dimethylphenyl)-1-3-[(E)-3-(4-methoxyphenyl)-2-propenoyl]phenyl-2,3-dihydro-1H-2-imidazolone
(7i) 1-3-[(E)-3-(4-methoxyphenyl)-2-propenoyl]phenyl-4-(3,4,5-trimethylphenyl)-2,3-dihydro-1H-2-imidazolone
(7j) 4-(4-hydroxyphenyl)-1-3-[(E)-3-(4-methoxyphenyl)-2-propenoyl]phenyl-2,3-dihydro-1H-2-imidazolone
(8a) 4-phenyl-1-3-[(E)-3-phenyl-2-propenoyl]phenyl-2,3-dihydro-1H-2-imidazolone
(8b) 4-(4-methoxyphenyl)-1-3-[(E)-3-phenyl-2-propenoyl]phenyl-2,3-dihydro-1H-2-imidazolone
(8c) 4-(3,4-dimethoxyphenyl)-1-3-[(E)-3-phenyl-2-propenoyl]phenyl-2,3-dihydro-1H-2-imidazolone
(8d) 1-3-[(E)-3-phenyl-2-propenoyl]phenyl-4-(3,4,5-trimethoxyphenyl)-2,3-dihydro-1H-2-imidazolone
(8e) 4-(4-fluorophenyl)-1-3-[(E)-3-phenyl-2-propenoyl]phenyl-2,3-dihydro-1H-2-imidazolone
(8f) 4-(4-chlorophenyl)-1-3-[(E)-3-phenyl-2-propenoyl]phenyl-2,3-dihydro-1H-2-imidazolone
(8g) 4-(4-methylphenyl)-1-3-[(E)-3-phenyl-2-propenoyl]phenyl-2,3-dihydro-1H-2-imidazolone
(8h) 4-(3,4-dimethylphenyl)-1-3-[(E)-3-phenyl-2-propenoyl]phenyl-2,3-dihydro-1H-2-imidazolone
(8i) 1-3-[(E)-3-phenyl-2-propenoyl]phenyl-4-(3,4,5-trimethylphenyl)-2,3-dihydro-1H-2-imidazolone
(8j) 4-(4-hydroxyphenyl)-1-3-[(E)-3-phenyl-2-propenoyl]phenyl-2,3-dihydro-1H-2-imidazolone
(9a) 1-3-[(E)-3-(4-fluorophenyl)-2-propenoyl]phenyl-4-phenyl-2,3-dihydro-1H-2-imidazolone
(9b) 1-3-[(E)-3-(4-fluorophenyl)-2-propenoyl]phenyl-4-(4-methoxyphenyl)-2,3-dihydro-1H-2-imidazolone
(9c) 4-(3,4-dimethoxyphenyl)-1-3-[(E)-3-(4-fluorophenyl)-2-propenoyl]phenyl-2,3-dihydro-1H-2-imidazolone
(9d) 1-3-[(E)-3-(4-fluorophenyl)-2-propenoyl]phenyl-4-(3,4,5-trimethoxyphenyl)-2,3-dihydro-1H-2-imidazolone
(9e) 4-(4-fluorophenyl)-1-3-[(E)-3-(4-fluorophenyl)-2-propenoyl]phenyl-2,3-dihydro-1H-2-imidazolone
(9f) 4-(4-chlorophenyl)-1-3-[(E)-3-(4-fluorophenyl)-2-propenoyl]phenyl-2,3-dihydro-1H-2-imidazolone
(9g) 1-3-[(E)-3-(4-fluorophenyl)-2-propenoyl]phenyl-4-(4-methylphenyl)-2,3-dihydro-1H-2-imidazolone
(9f) 4-(3,4-dimethylphenyl)-1-3-[(E)-3-(4-fluorophenyl)-2-propenoyl]phenyl-2,3-dihydro-1H-2-imidazolone
(9i) 1-3-[(E)-3-(4-fluorophenyl)-2-propenoyl]phenyl-4-(3,4,5-trimethylphenyl)-2,3-dihydro-1H-2-imidazolone
(9j) 1-3-[(E)-3-(4-fluorophenyl)-2-propenoyl]phenyl-4-(4-hydroxyphenyl)-2,3-dihydro-1H-2-imidazolone
(10a) 1-3-[(E)-3-(4-chlorophenyl)-2-propenoyl]phenyl-4-phenyl-2,3-dihydro-1H-2-imidazolone
(10b) 1-3-[(E)-3-(4-chlorophenyl)-2-propenoyl]phenyl-4-(4-methoxyphenyl)-2,3-dihydro-1H-2-imidazolone
(10c) 1-3-[(E)-3-(4-chlorophenyl)-2-propenoyl]phenyl-4-(3,4-dimethoxyphenyl)-2,3-dihydro-1H-2-imidazolone
(10d) 1-3-[(E)-3-(4-chlorophenyl)-2-propenoyl]phenyl-4-(3,4,5-trimethoxyphenyl)-2,3-dihydro-1H-2-imidazolone
(10e) 1-3-[(E)-3-(4-chlorophenyl)-2-propenoyl]phenyl-4-(4-fluorophenyl)-2,3-dihydro-1H-2-imidazolone
(10f) 4-(4-chlorophenyl)-1-3-[(E)-3-(4-chlorophenyl)-2-propenoyl]phenyl-2,3-dihydro-1H-2-imidazolone
(10g) 1-3-[(E)-3-(4-chlorophenyl)-2-propenoyl]phenyl-4-(4-methylphenyl)-2,3-dihydro-1H-2-imidazolone
(10h) 1-3-[(E)-3-(4-chlorophenyl)-2-propenoyl]phenyl-4-(3,4-dimethylphenyl)-2,3-dihydro-1H-2-imidazolone
(10i) 1-3-[(E)-3-(4-chlorophenyl)-2-propenoyl]phenyl-4-(3,4,5-trimethylphenyl)-2,3-dihydro-1H-2-imidazolone
(10j) 1-3-[(E)-3-(4-chlorophenyl)-2-propenoyl]phenyl-4-(4-hydroxyphenyl)-2,3-dihydro-1H-2-imidazolone
(11a) 1-3-[(E)-3-(4-hydroxy-3,5-dimethoxyphenyl)-2-propenoyl]phenyl-4-phenyl-2,3-dihydro-1H-2-imidazolone
(11b) 1-3-[(E)-3-(4-hydroxy-3,5-dimethoxyphenyl)-2-propenoyl]phenyl-4-(4-methoxyphenyl)-2,3-dihydro-1H-2-imidazolone
(11c) 4-(3,4-dimethoxyphenyl)-1-3-[(E)-3-(4-hydroxy-3,5-dimethoxyphenyl)-2-propenoyl]phenyl-2,3-dihydro-1H-2-imidazolone (11d) 1-3-[(E)-3-(4-hydroxy-3,5-dimethoxyphenyl)-2-propenoyl]phenyl-4-(3,4,5-trimethoxyphenyl)-2,3-dihydro-1H-2-imidazolone
(11e) 4-(4-fluorophenyl)-1-3-[(E)-3-(4-hydroxy-3,5-dimethoxyphenyl)-2-propenoyl]phenyl-2,3-dihydro-1H-2-imidazolone
(11f) 4-(4-chlorophenyl)-1-3-[(E)-3-(4-hydroxy-3,5-dimethoxyphenyl)-2-propenoyl]phenyl-2,3-dihydro-1H-2-imidazolone
(11g) 1-3-[(E)-3-(4-hydroxy-3,5-dimethoxyphenyl)-2-propenoyl]phenyl-4-(4-methylphenyl)-2,3-dihydro-1H-2-imidazolone
(11h) 4-(3,4-dimethylphenyl)-1-3-[(E)-3-(4-hydroxy-3,5-dimethoxyphenyl)-2-propenoyl]phenyl-2,3-dihydro-1H-2-imidazolone
(11i) 1-3-[(E)-3-(4-hydroxy-3,5-dimethoxyphenyl)-2-propenoyl]phenyl-4-(3,4,5-trimethylphenyl)-2,3-dihydro-1H-2-imidazolone
(11j) 1-3-[(E)-3-(4-hydroxy-3,5-dimethoxyphenyl)-2-propenoyl]phenyl-4-(4-hydroxyphenyl)-2,3-dihydro-1H-2-imidazolone
(12a) 1-3-[(E)-3-(4-hydroxy-3-methoxyphenyl)-2-propenoyl]phenyl-4-(2-naphthyl)-2,3-dihydro-1H-2-imidazolone
(12b) 1-3-[(E)-3-(3-hydroxyphenyl)-2-propenoyl]phenyl-4-(2-naphthyl)-2,3-dihydro-1H-2-imidazolone
(12c) 4-(2-naphthyl)-1-3-[(E)-3-(3,4,5-trimethoxyphenyl)-2-propenoyl]phenyl-2,3-dihydro-1H-2-imidazolone
(12d) 1-3-[(E)-3-(3,4-dimethoxyphenyl)-2-propenoyl]phenyl-4-(2-naphthyl)-2,3-dihydro-1H-2-imidazolone
(12e) 1-3-[(E)-3-(4-methoxyphenyl)-2-propenoyl]phenyl-4-(2-naphthyl)-2,3-dihydro-1H-2-imidazolone
(12f) 4-(2-naphthyl)-1-3-[(E)-3-phenyl-2-propenoyl]phenyl-2,3-dihydro-1H-2-imidazolone
(12g) 1-3-[(E)-3-(4-fluorophenyl)-2-propenoyl]phenyl-4-(2-naphthyl)-2,3-dihydro-1H-2-imidazolone
(12h) 1-3-[(E)-3-(4-chlorophenyl)-2-propenoyl]phenyl-4-(2-naphthyl)-2,3-dihydro-1H-2-imidazolone
(12i) 1-3-[(E)-3-(4-hydroxy-3,5-dimethoxyphenyl)-2-propenoyl]phenyl-4-(2-naphthyl)-2,3-dihydro-1H-2-imidazolone
(13a) 1-3-[(E)-3-(4-hydroxy-3-methoxyphenyl)-2-propenoyl]phenyl-4-(3-pyridyl)-2,3-dihydro-1H-2-imidazolone
(13b) 1-3-[(E)-3-(3-hydroxyphenyl)-2-propenoyl]phenyl-4-(3-pyridyl)-2,3-dihydro-1H-2-imidazolone
(13c) 4-(3-pyridyl)-1-3-[(E)-3-(3,4,5-trimethoxyphenyl)-2-propenoyl]phenyl-2,3-dihydro-1H-2-imidazolone
(13d) 1-3-[(E)-3-(3,4-dimethoxyphenyl)-2-propenoyl]phenyl-4-(3-pyridyl)-2,3-dihydro-1H-2-imidazolone
(13e) 1-3-[(E)-3-(4-methoxyphenyl)-2-propenoyl]phenyl-4-(3-pyridyl)-2,3-dihydro-1H-2-imidazolone
(13f) 1-3-[(E)-3-phenyl-2-propenoyl]phenyl-4-(3-pyridyl)-2,3-dihydro-1H-2-imidazolone
(13g) 1-3-[(E)-3-(4-fluorophenyl)-2-propenoyl]phenyl-4-(3-pyridyl)-2,3-dihydro-1H-2-imidazolone
(13h) 1-3-[(E)-3-(4-chlorophenyl)-2-propenoyl]phenyl-4-(3-pyridyl)-2,3-dihydro-1H-2-imidazolone
(13i) 1-3-[(E)-3-(4-hydroxy-3,5-dimethoxyphenyl)-2-propenoyl]phenyl-4-(3-pyridyl)-2,3-dihydro-1H-2-imidazolone
(14a) 4-(2-furyl)-1-3-[(E)-3-(4-hydroxy-3-methoxyphenyl)-2-propenoyl]phenyl-2,3-dihydro-1H-2-imidazolone
(14b) 4-(2-furyl)-1-3-[(E)-3-(3-hydroxyphenyl)-2-propenoyl]phenyl-2,3-dihydro-1H-2-imidazolone
(14c) 4-(2-furyl)-1-3-[(E)-3-(3,4,5-trimethoxyphenyl)-2-propenoyl]phenyl-2,3-dihydro-1H-2-imidazolone
(14d) 1-3-[(E)-3-(3,4-dimethoxyphenyl)-2-propenoyl]phenyl-4-(2-furyl)-2,3-dihydro-1H-2-imidazolone
(14e) 4-(2-furyl)-1-3-[(E)-3-(4-methoxyphenyl)-2-propenoyl]phenyl-2,3-dihydro-1H-2-imidazolone
(14f) 4-(2-furyl)-1-3-[(E)-3-phenyl-2-propenoyl]phenyl-2,3-dihydro-1H-2-imidazolone
(14g) 1-3-[(E)-3-(4-fluorophenyl)-2-propenoyl]phenyl-4-(2-furyl)-2,3-dihydro-1H-2-imidazolone
(14h) 1-3-[(E)-3-(4-chlorophenyl)-2-propenoyl]phenyl-4-(2-furyl)-2,3-dihydro-1H-2-imidazolone
(14i) 4-(2-furyl)-1-3-[(E)-3-(4-hydroxy-3,5-dimethoxyphenyl)-2-propenoyl]phenyl-2,3-dihydro-1H-2-imidazolone
(15a) 4-(5-chloro-2-furyl)-1-3-[(E)-3-(4-hydroxy-3-methoxyphenyl)-2-propenoyl]phenyl-2,3-dihydro-1H-2-imidazolone
(15b) 4-(5-chloro-2-furyl)-1-3-[(E)-3-(3-hydroxyphenyl)-2-propenoyl]phenyl-2,3-dihydro-1H-2-imidazolone
(15c) 4-(5-chloro-2-furyl)-1-3-[(E)-3-(3,4,5-trimethoxyphenyl)-2-propenoyl]phenyl-2,3-dihydro-1H-2-imidazolone
(15d) 4-(5-chloro-2-furyl)-1-3-[(E)-3-(3,4-diethoxyphenyl)-2-propenoyl]phenyl-2,3-dihydro-1H-2-imidazolone
(15e) 4-(5-chloro-2-furyl)-1-3-[(E)-3-(4-methoxyphenyl)-2-propenoyl]phenyl-2,3-dihydro-1H-2-imidazolone
(15f) 4-(5-chloro-2-furyl)-1-3-[(E)-3-phenyl-2-propenoyl]phenyl-2,3-dihydro-1H-2-imidazolone
(15g) 4-(5-chloro-2-furyl)-1-3-[(E)-3-(4-fluorophenyl)-2-propenoyl]phenyl-2,3-dihydro-1H-2-imidazolone
(15h) 4-(5-chloro-2-furyl)-1-3-[(E)-3-(4-chlorophenyl)-2-propenoyl]phenyl-2,3-dihydro-1H-2-imidazolone
(15i) 4-(5-chloro-2-furyl)-1-3-[(E)-3-(4-hydroxy-3,5-dimethoxyphenyl)-2-propenoyl]phenyl-2,3-dihydro-1H-2-imidazolone
(16a) 1-3-[(E)-3-(4-hydroxy-3-methoxyphenyl)-2-propenoyl]phenyl-4-(5-methyl-2-furyl)-2,3-dihydro-1H-2-imidazolone
(16b) 1-3-[(E)-3-(3-hydroxyphenyl)-2-propenoyl]phenyl-4-(5-methyl-2-furyl)-2,3-dihydro-1H-2-imidazolone
(16c) 4-(5-methyl-2-furyl)-1-3-[(E)-3-(3,4,5-trimethoxyphenyl)-2-propenoyl]phenyl-2,3-dihydro-1H-2-imidazolone
(16d) 1-3-[(E)-3-(3,4-dimethoxyphenyl)-2-propenoyl]phenyl-4-(5-methyl-2-furyl)-2,3-dihydro-1H-2-imidazolone
(16e) 1-3-[(E)-3-(4-methoxyphenyl)-2-propenoyl]phenyl-4-(5-methyl-2-furyl)-2,3-dihydro-1H-2-imidazolone
(16f) 4-(5-methyl-2-furyl)-1-3-[(E)-3-phenyl-2-propenoyl]phenyl-2,3-dihydro-1H-2-imidazolone
(16g) 1-3-[(E)-3-(4-fluorophenyl)-2-propenoyl]phenyl-4-(5-methyl-2-furyl)-2,3-dihydro-1H-2-imidazolone
(16h) 1-3-[(E)-3-(4-chlorophenyl)-2-propenoyl]phenyl-4-(5-methyl-2-furyl)-2,3-dihydro-1H-2-imidazolone
(16i) 1-3-[(E)-3-(4-hydroxy-3,5-dimethoxyphenyl)-2-propenoyl]phenyl-4-(5-methyl-2-furyl)-2,3-dihydro-1H-2-imidazolone
(17a) 1-3-[(E)-3-(4-hydroxy-3-methoxyphenyl)-2-propenoyl]phenyl-4-(2-thienyl)-2,3-dihydro-1H-2-imidazolone
(17b) 1-3-[(E)-3-(3-hydroxyphenyl)-2-propenoyl]phenyl-4-(2-thienyl)-2,3-dihydro-1H-2-imidazolone
(17c) 4-(2-thienyl)-1-3-[(E)-3-(3,4,5-trimethoxyphenyl)-2-propenoyl]phenyl-2,3-dihydro-1H-2-imidazolone
(17d) 1-3-[(E)-3-(3,4-dimethoxyphenyl)-2-propenoyl]phenyl-4-(2-thienyl)-2,3-dihydro-1H-2-imidazolone
(17e) 1-3-[(E)-3-(4-methoxyphenyl)-2-propenoyl]phenyl-4-(2-thienyl)-2,3-dihydro-1H-2-imidazolone
(17f) 1-3-[(E)-3-phenyl-2-propenoyl]phenyl-4-(2-thienyl)-2,3-dihydro-1H-2-imidazolone
(17g) 1-3-[(E)-3-(4-fluorophenyl)-2-propenoyl]phenyl-4-(2-thienyl)-2,3-dihydro-1H-2-imidazolone (17h) 1-3-[(E)-3-(4-chlorophenyl)-2-propenoyl]phenyl-4-(2-thienyl)-2,3-dihydro-1H-2-imidazolone
(17i) 1-3-[(E)-3-(4-hydroxy-3,5-dimethoxyphenyl)-2-propenoyl]phenyl-4-(2-thienyl)-2,3-dihydro-1H-2-imidazolone
(18a) 4-(5-chloro-2-thienyl)-1-3-[(E)-3-(4-hydroxy-3-methoxyphenyl)-2-propenoyl]phenyl-2,3-dihydro-1H-2-imidazolone
(18b) 4-(5-chloro-2-thienyl)-1-3-[(E)-3-(3-hydroxyphenyl)-2-propenoyl]phenyl-2,3-dihydro-1H-2-imidazolone
(18c) 4-(5-chloro-2-thienyl)-1-3-[(E)-3-(3,4,5-trimethoxyphenyl)-2-propenoyl]phenyl-2,3-dihydro-1H-2-imidazolone
(18d) 4-(5-chloro-2-thienyl)-1-3-[(E)-3-(3,4-dimethoxyphenyl)-2-propenoyl]phenyl-2,3-dihydro-1H-2-imidazolone
(18e) 4-(5-chloro-2-thienyl)-1-3-[(E)-3-(4-methoxyphenyl)-2-propenoyl]phenyl-2,3-dihydro-1H-2-imidazolone
(18f) 4-(5-chloro-2-thienyl)-1-3-[(E)-3-phenyl-2-propenoyl]phenyl-2,3-dihydro-1H-2-imidazolone
(18g) 4-(5-chloro-2-thienyl)-1-3-[(E)-3-(4-fluorophenyl)-2-propenoyl]phenyl-2,3-dihydro-1H-2-imidazolone
(18h) 1-3-[(E)-3-(4-chlorophenyl)-2-propenoyl]phenyl-4-(5-chloro-2-thienyl)-2,3-dihydro-1H-2-imidazolone
(18i) 4-(5-chloro-2-thienyl)-1-3-[(E)-3-(4-hydroxy-3,5-dimethoxyphenyl)-2-propenoyl]phenyl-2,3-dihydro-1H-2-imidazolone
(19a) 1-3-[(E)-3-(4-hydroxy-3-methoxyphenyl)-2-propenoyl]phenyl-4-(5-methyl-2-thienyl)-2,3-dihydro-1H-2-imidazolone
(19b) 1-3-[(E)-3-(3-hydroxyphenyl)-2-propenoyl]phenyl-4-(5-methyl-2-thienyl)-2,3-dihydro-1H-2-imidazolone
(19c) 4-(5-methyl-2-thienyl)-1-3-[(E)-3-(3,4,5-trimethoxyphenyl)-2-propenoyl]phenyl-2,3-dihydro-1H-2-imidazolone
(19d) 1-3-[(E)-3-(3,4-dimethoxyphenyl)-2-propenoyl]phenyl-4-(5-methyl-2-thienyl)-2,3-dihydro-1H-2-imidazolone
(19e) 1-3-[(E)-3-(4-methoxyphenyl)-2-propenoyl]phenyl-4-(5-methyl-2-thienyl)-2,3-dihydro-1H-2-imidazolone
(19f) 4-(5-methyl-2-thienyl)-1-3-[(E)-3-phenyl-2-propenoyl]phenyl-2,3-dihydro-1H-2-imidazolone
(19g) 1-3-[(E)-3-(4-fluorophenyl)-2-propenoyl]phenyl-4-(5-methyl-2-thienyl)-2,3-dihydro-1H-2-imidazolone
(19h) 1-3-[(E)-3-(4-chlorophenyl)-2-propenoyl]phenyl-4-(5-methyl-2-thienyl)-2,3-dihydro-1H-2-imidazolone
(19i) 1-3-[(E)-3-(4-hydroxy-3,5-dimethoxyphenyl)-2-propenoyl]phenyl-4-(5-methyl-2-thienyl)-2,3-dihydro-1H-2-imidazolone In still another embodiment of the present invention, process for the preparation of Chalcone linked imidazolone compounds of formula A

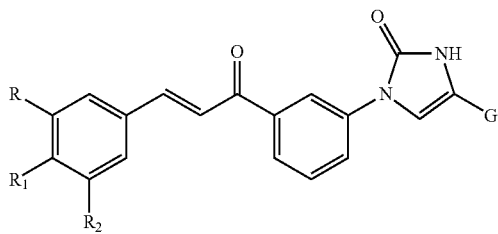

Formula A

Wherein

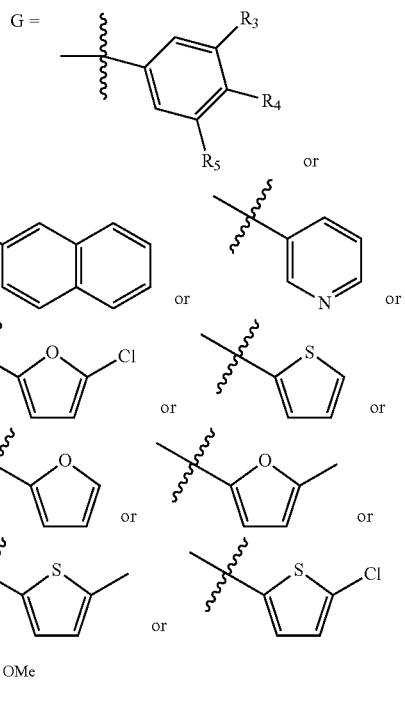

R = H, OMe
$R_1$ = H, Cl, F, OH, OMe
$R_2$ = H, OH, OMe
$R_3$ = H, OMe, $CH_3$
$R_4$ = H, Cl, F, OH, OMe, $CH_3$
$R_5$ = H, OMe, $CH_3$ and the said process comprising the steps of:
i. stirring the solution of $Ba(OH)_2.8H_2O$, NaOH in methanol or ethanol;
ii. adding 3-aminoacetophenone 2 and aldehyde 1a-i wherein R represent hydrogen and methoxy, R1 represent hydrogen, methoxy, hydroxy, chloro and fluoro and R2 represent hydrogen, methoxy and hydroxy in the stirred solution obtained in step i to obtain intermediate 20a-i (chalconoamines) wherein R represent hydrogen and methoxy, R1 represent hydrogen, methoxy, hydroxy, chloro and fluoro and R2 represent hydrogen, methoxy and hydroxy;

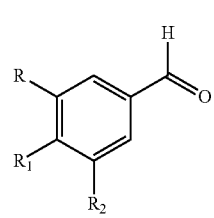

1a-i

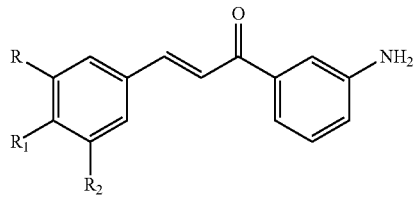

20a-i iii. reacting (E)-3-(3-aminophenyl)-1-phenyl-2-propen-1-one of formula 20a-i (chalconoamines) with the substituted phenacyl bromide of formula 21a-j, 22, 23, 23 to 29 in the presence of sodium bicarbonate in ethanol and methanol to obtain N-arylphenacylamines 30a-j to 38a-j and 39a-i to 46a-i;

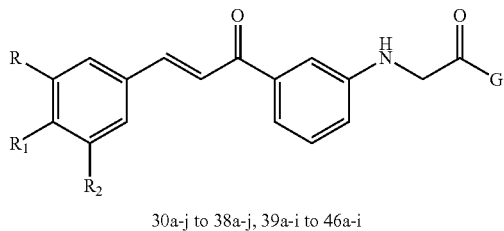

30a-j to 38a-j, 39a-i to 46a-i iv. stirring the mixture of N-arylphenacylamine 30a-j to 38a-j and 39a-i to 46a-i and potassium cyanate in acetic acid;
v. purifying by column chromatography using MeOH—CHCl$_3$ to give final compounds 3a-j to 11a-j, 12a-i to 19a-i.

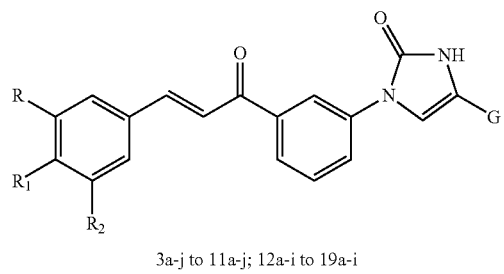

3a-j to 11a-j; 12a-i to 19a-i

BRIEF DESCRIPTION OF THE DRAWING(S)

DETAILED DESCRIPTION OF THE INVENTION

Figure 1:
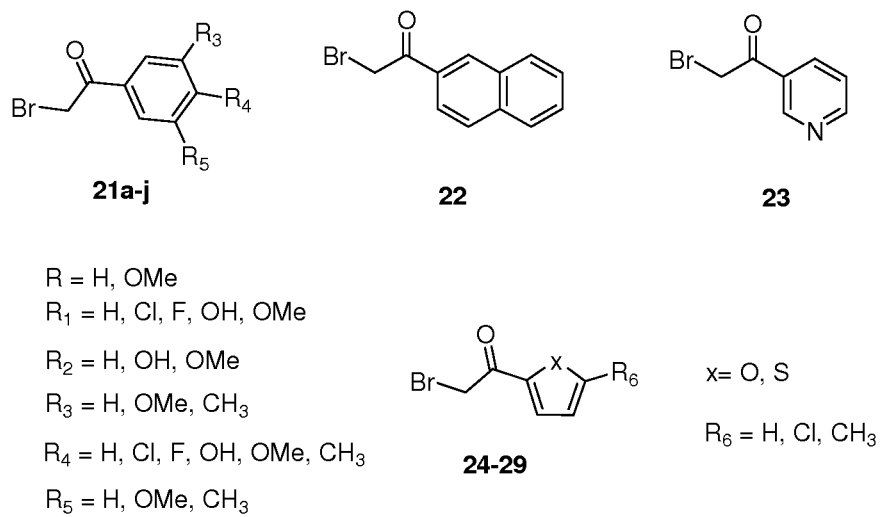
FIG. 1 depicts substituted phenacyl bromides of formula 21a-j, 22, 23, 23 to 29 that are used in the synthesis of N-arylphenacylamines intermediates from chalconamine intermediates during the synthesis of Chalcone linked Imidazolones of the present invention.
Figure 2:
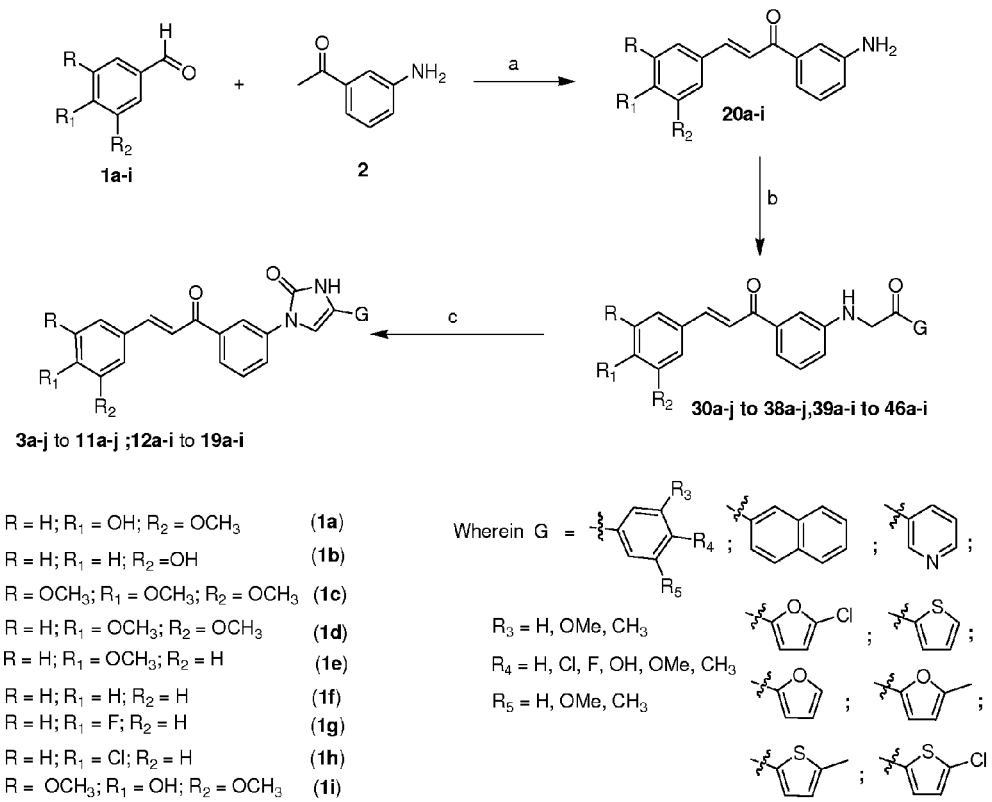
FIG. 2 shows synthesis of Chalcone linked Imidazolones of the present invention as illustrated in Scheme-1.

Chalcone linked Imidazolones have shown promising anticancer activity in various cell lines. The molecules synthesized are of immense biological significance with potential inhibition of tubulin polymerization. This resulted in design and synthesis of new congeners as illustrated in Scheme-1, which comprise:

1. Condensation reaction between 3-aminoacetophenones and aldehydes
2. Coupling reaction between substituted chalcone amines and the phenacyl bromides.
3. Imidazolone ring formation occurred at 65° C. for 2 h.
4. Synthesis of new hybrids of chalcone-imidazolone as anticancer and inhibitors of tubulin polymerization.
5. Purification by column chromatography using different solvents like ethyl acetate, hexane, chloroform and methanol.

EXAMPLES

The present invention will be more specifically explained by following examples. However, the scope of the present invention is not limited to the scope of these examples below.

Example-1

3-Amino-acetophenone (1.0 mmol, 270 mg) was added to a suspension of barium hydroxide octahydrate (1.5 mmol, 945 mg) in methanol (15 mL), and the mixture was stirred for 5 min. Then a solution of vanillin (1 mmol, 304 mg) in methanol (10 mL) was added, and the resulting mixture was stirred for overnight at 27° C. After completion of the reaction as indicated by TLC, the solvent was removed under vacuum and aqueous layer then extracted with ethylacetate (3×30 mL). The combined organic phase was dried over Na$_2$SO$_4$ and evaporated under vacuum to afford the crude (E)-1-(3-aminophenyl)-3-(4-hydroxy-3-methoxyphenyl)-2-propen-1-one. The crude product thus obtained was purified by column chromatography using EtoAC-Hexane (30%) as eluent to afford pure compound of 20a (322.8 mg 60%)

Coupling of compound 20a (1.0 mmol, 538 mg) with phenacyl bromide 21a (1.5 mmol, 597 mg) in the presence of sodium bicarbonate (2.0 mmol, 336 mg) in ethanol, afforded N-arylphenacylamine 30a, which was used directly in the next step.

A mixture of compound 30a (1.0 mmol, 772 mg) and potassium cyanate (1.5 mmol, 243 mg) in acetic acid (5 mL) was stirred for 1.5 h at 60-65° C. After cooling, water (25 mL) was added. The insoluble product was filtered off and washed with water, then with cold methanol. The crude product was purified by column chromatography using MeOH—CHCl$_3$ (4%) to give compound 3a (535 mg, 65%)
$^1$H NMR (CDCl$_3$): δ 3.86 (s, 3H), 6.89 (d, 1H), 7.18-7.27 (m, 3H), 7.38 (t, 3H), 7.58-7.65 (m, 4H), 7.72 (d, 1H, J=15.2 Hz), 7.90 (d, 1H), 8.06 (d, 1H), 8.38 (s, 1H), 9.39 (s, 1H), 11.10 (s, 1H), FABMS: 435 (M$^+$+23)

Example-2

3-Amino-acetophenone (1.0 mmol, 270 mg) was added to a suspension of barium hydroxide octahydrate (1.5 mmol, 945 mg) in methanol (15 mL), and the mixture was stirred for 5 min. Then a solution of vanillin (1 mmol, 304 mg) in methanol (10 mL) was added, and the resulting mixture was stirred for overnight at 27° C. After completion of the reaction as indicated by TLC, the solvent was removed under vacuum and aqueous layer then extracted with ethylacetate (3×30 mL). The combined organic phase was dried over Na$_2$SO$_4$ and evaporated under vacuum to afford the crude (E)-1-(3-aminophenyl)-3-(4-hydroxy-3-methoxyphenyl)-2-propen-1-one. The crude product thus obtained was purified by column chromatography using EtoAC-Hexane (30%) as eluent to afford pure compound of 20a (322.8 mg 60%)

Coupling of compound 20a (1.0 mmol, 538 mg) with phenacyl bromide 21b (1.5 mmol, 597 mg) in the presence of sodium bicarbonate (2.0 mmol, 336 mg) in ethanol, afforded N-arylphenacylamine 30b, which was used directly in the next step.

A mixture of compound 30b (1.0 mmol, 774 mg) and potassium cyanate (15 mmol, 243 mg) in acetic acid (5 mL) was stirred for 1.5 h at 60-65° C. After cooling, water (25 mL) was added. The insoluble product was filtered off and washed with water, then with cold methanol. The crude product was purified by column chromatography using MeOH—CHCl$_3$ (4%) to give compound 3b (494 mg, 60%)

$^1$H NMR (CDCl$_3$): δ 3.87 (s, 3H), 4.02 (s, 3H), 6.86 (d, 1H), 7.04-7.23 (m, 2H), 7.32 (d, 2H), 7.48-7.70 (m, 4H), 7.92 (d, 2H), 8.06 (d, 1H), 8.34 (s, 1H), 11.10 (s, 1H) FABMS: m/z 465 (M$^+$+23).

Example-3

3-Amino-acetophenone (2) (1.0 mmol, 270 mg) was added to a suspension of barium hydroxide octahydrate (1.5 mmol, 945 mg) in methanol (15 mL), and the mixture was stirred for 5 min. Then a solution of vanillin (1 mmol, 304 mg) in methanol (10 mL) was added, and the resulting mixture was stirred for overnight at 27° C. After completion of the reaction as indicated by TLC, the solvent was removed under vacuum and aqueous layer then extracted with ethylacetate (3×30 mL). The combined organic phase was dried over Na$_2$SO$_4$ and evaporated under vacuum to afford the crude (E)-1-(3-aminophenyl)-3-(4-hydroxy-3-methoxyphenyl)-2-propen-1-one. The crude product thus obtained was purified by column chromatography using EtoAC-Hexane (30%) as eluent to afford pure compound of 20a (322.8 mg 60%)

Coupling of compound 20a (1.0 mmol, 538 mg) with phenacyl bromide 21f (1.5 mmol, 597 mg) in the presence of sodium bicarbonate (2.0 mmol, 336 mg) in ethanol, afforded N-arylphenacylamine 30f, which was used directly in the next step.

A mixture of compound 30f (1.0 mmol, 834 mg) and potassium cyanate (1.5 mmol, 243 mg) in acetic acid (5 mL) was stirred for 1.5 h at 60-65° C. After cooling, water (25 mL) was added. The insoluble product was filtered off and washed with water, then with cold methanol. The crude product was purified by column chromatography using MeOH—CHCl$_3$ (4%) to give compound 3f (592 mg, 67%)

$^1$H NMR (CDCl$_3$+DMSO): δ 3.87 (s, 3H), 6.87 (d, 1H), 6.95 (s, 1H), 7.06-7.12 (m, 2H), 7.24-7.55 (m, 6H), 7.65 (s, 1H), 7.77 (t, 1H), 3.78-3.92 (m, 6H), 7.92 (d, 1H), 8.12 (s, 1H), 10.93 (s, 1H), ESIMS: m/z 470 (M$^+$+23).

Example-4

3-Amino-acetophenone (1.0 mmol, 270 mg) was added to a suspension of barium hydroxide octahydrate (1.5 mmol, 945 mg) in methanol (15 mL), and the mixture was stirred for 5 min. Then a solution of vanillin (1 mmol, 304 mg) in methanol (10 mL) was added, and the resulting mixture was stirred for overnight at 27° C. After completion of the reaction as indicated by TLC, the solvent was removed under vacuum and aqueous layer then extracted with ethylacetate (3×30 mL). The combined organic phase was dried over Na$_2$SO$_4$ and evaporated under vacuum to afford the crude (E)-1-(3-aminophenyl)-3-(4-hydroxy-3-methoxyphenyl)-2-propen-1-one. The crude product thus obtained was purified by column chromatography using EtoAC-Hexane (30%) as eluent to afford pure compound of 20a (322.8 mg 60%)

Coupling of compound 20a (1.0 mmol, 538 mg) with phenacyl bromide 21d (1.5 mmol, 597 mg) in the presence of sodium bicarbonate (2.0 mmol, 336 mg) in ethanol, afforded N-arylphenacylamine 30d, which was used directly in the next step.

A mixture of compound 30d (1.0 mmol, 812 mg) and potassium cyanate (1.5 mmol, 243 mg) in acetic acid (5 mL) was stirred for 1.5 h at 60-65° C. After cooling, water (25 mL) was added. The insoluble product was filtered off and washed with water, then with cold methanol. The crude product was purified by column chromatography using MeOH—CHCl$_3$ (4%) to give compound 3d (646 mg, 75%)

$^1$H NMR (CDCl$_3$+DMSO): δ 6.88 (d, 1H), 7.10-7.25 (m, 2H), 7.42-7.45 (m, 3H), 7.57-7.70 (m, 5H), 7.84-7.87 (m, 4H), 8.10 (s, 1H), 8.16 (d, 1H), 8.44 (s, 1H), 11.24 (s, 1H) FABMS: m/z 455 (M$^+$+23).

Biological Activity

Some of biological activity studies were carried out at the National Cancer Institute (NCI), Maryland, USA.

Anticancer Activity:

The compounds were evaluated for anticancer activity against fifty three human cancer cells derived from nine cancer types (leukemia cell line, non-small-cell lung cell line, colon cell line, CNS cell line, melanoma cell line, ovarian cell line, prostate cell line, and breast cancer cell line) as shown in Table 1. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth.

TABLE 1

| Cancer panel/cell line | GI$_{50}$ (μm) | | | | | | | | | |
|---|---|---|---|---|---|---|---|---|---|---|
| | 3a | 3b | 3f | 4a | 4f | 5a | 5b | 5d | 5f | 12b |
| Leukemia | | | | | | | | | | |
| RPMI-8226 | 1.67 | 1.35 | 1.33 | 2.15 | 1.55 | 0.62 | 0.92 | 0.23 | 3.92 | 1.67 |
| K-562 | 2.04 | 2.35 | 1.42 | 3.35 | 0.40 | 0.50 | 1.27 | 0.59 | 3.69 | 1.43 |
| Non-small cell lung | | | | | | | | | | |
| A549/ATCC | 3.85 | 4.14 | 6.78 | 3.89 | 3.55 | 4.03 | 11.8 | 3.03 | 85.2 | 3.38 |
| EKVX | 3.90 | 13.4 | 9.61 | 15.6 | 2.40 | 2.30 | 4.20 | 9.47 | na | 2.64 |
| HOP-62 | 1.48 | 5.15 | 2.84 | 6.93 | 2.36 | 4.12 | 5.91 | 3.08 | na | 2.26 |
| HOP-92 | 2.27 | 2.96 | 1.26 | 5.04 | 1.60 | 10.8 | 14.9 | nt | na | 0.51 |
| NCI-H226 | 2.60 | 4.10 | 2.77 | 24.8 | 2.31 | 14.6 | 35.2 | 14.4 | na | 2.43 |
| NCI-H23 | 2.02 | 2.85 | 3.18 | 3.35 | 2.78 | 1.43 | 1.63 | 2.00 | 3.56 | 1.52 |
| NCI-H322M | 3.39 | 8.20 | 4.58 | 10.6 | 2.52 | 2.02 | 2.66 | 3.61 | 12.9 | 1.66 |
| NCI-H460 | 1.95 | 3.23 | 3.90 | 2.49 | 2.41 | 1.40 | 1.56 | 1.73 | 3.74 | 1.67 |
| NCI-H522 | 2.36 | 3.48 | 2.36 | nt | 1.65 | 0.95 | 1.85 | 1.05 | 4.10 | 1.29 |
| Colon | | | | | | | | | | |
| COLO 205 | 2.21 | 6.61 | 3.40 | 2.01 | 2.29 | 1.51 | 1.84 | 1.52 | 7.38 | 2.09 |
| HCC-2998 | 1.51 | 2.32 | 1.85 | 4.09 | 13.7 | 1.26 | 1.64 | 1.92 | 2.46 | 2.13 |
| HCT-116 | 1.40 | 1.93 | 1.46 | 3.02 | 1.23 | 0.33 | 0.37 | 0.74 | 1.39 | 0.40 |
| HCT-15 | 2.73 | 3.15 | 1.80 | 3.10 | 2.33 | 1.13 | 1.38 | 1.89 | 3.85 | 1.56 |
| HT29 | 3.77 | 3.84 | 2.97 | 3.33 | 1.90 | 0.66 | 1.28 | 1.70 | 2.00 | 1.54 |
| KM12 | 1.61 | 1.77 | 1.48 | 1.83 | 1.34 | 1.37 | 1.42 | 1.12 | 5.45 | 1.21 |
| SW-620 | 2.29 | 2.50 | 2.00 | 2.41 | 1.62 | 0.39 | 0.45 | 1.03 | 1.75 | 0.22 |
| CNS | | | | | | | | | | |
| SF-268 | 2.07 | 3.40 | 2.50 | 4.53 | 1.78 | 1.92 | 3.21 | 2.20 | 5.07 | 1.73 |

TABLE 1-continued

| Cancer panel/cell line | GI$_{50}$ (μm) | | | | | | | | | |
|---|---|---|---|---|---|---|---|---|---|---|
| | 3a | 3b | 3f | 4a | 4f | 5a | 5b | 5d | 5f | 12b |
| SF-295 | 3.04 | 13.9 | 10.5 | 18.2 | 1.79 | 1.90 | 4.95 | 4.96 | 24.3 | 1.44 |
| SF-539 | 1.91 | 2.25 | 1.78 | 1.98 | 1.68 | 1.68 | 2.00 | 3.12 | 3.49 | 1.55 |
| SNB-19 | 2.96 | 5.84 | 3.17 | 10.9 | 1.92 | 2.35 | 4.38 | 4.07 | 16.1 | 1.32 |
| SNB-75 | 3.90 | 4.73 | 2.75 | 12.1 | 1.46 | 4.47 | 4.59 | 5.13 | na | 1.88 |
| U251 | 2.11 | 3.45 | 2.23 | 1.61 | 0.58 | 0.63 | 0.88 | 1.23 | 2.12 | 1.09 |
| Renal | | | | | | | | | | |
| A498 | 1.68 | 3.72 | 2.82 | 14.3 | 3.71 | 2.65 | 4.21 | 20.3 | 30.2 | nt |
| 786-0 | 1.35 | 4.53 | 2.07 | 2.98 | 1.57 | 1.38 | 1.61 | 1.59 | 2.14 | 1.74 |
| ACHN | 2.50 | 3.40 | 2.19 | 2.76 | 1.84 | 1.60 | 1.82 | 1.74 | 7.17 | 1.57 |
| CAKI-1 | 2.19 | 4.99 | 2.64 | 13.3 | 1.72 | 1.75 | 3.05 | 2.89 | na | 1.45 |
| RXF 393 | 2.27 | 5.85 | 6.40 | 1.89 | 1.51 | 1.71 | 1.92 | 1.62 | 3.22 | 1.41 |
| SN12C | 3.31 | 4.11 | 2.87 | 3.14 | 1.95 | 2.09 | 3.50 | 2.75 | 5.14 | 1.44 |
| TK-10 | 5.29 | 6.08 | 4.67 | nt | 2.83 | 3.02 | 3.04 | 3.00 | 6.46 | 3.45 |
| UO-31 | 2.18 | 5.19 | 1.67 | 2.16 | 0.55 | 1.51 | 1.91 | 0.96 | 7.03 | 1.26 |
| Prostate | | | | | | | | | | |
| PC-3 | 2.52 | 3.05 | 1.95 | 2.82 | nt | 3.26 | 6.22 | 2.63 | na | 1.85 |
| Ovarian | | | | | | | | | | |
| OVCAR-3 | 2.29 | 2.70 | 1.56 | 3.08 | 1.56 | 1.23 | 1.78 | 1.48 | 2.40 | 1.33 |
| OVCAR-4 | 5.19 | 6.08 | 4.64 | 5.30 | 2.21 | 1.88 | 3.57 | 3.77 | 11.4 | 1.68 |
| OVCAR-5 | 2.04 | 3.38 | 2.00 | 5.44 | 2.19 | 1.88 | 2.64 | 4.38 | 3.11 | 1.89 |
| OVCAR-8 | 4.11 | 4.97 | 4.18 | 2.80 | 0.99 | 1.62 | 2.53 | 2.32 | 3.85 | 2.33 |
| NCI/ADR-RES | 2.92 | 2.56 | 2.28 | 3.73 | 2.20 | 1.10 | 1.70 | 2.10 | 2.36 | 1.55 |
| SK-OV-3 | 3.76 | 4.77 | 3.19 | 11.1 | 4.21 | 3.27 | 4.60 | 5.12 | 31.4 | 2.15 |
| Breast | | | | | | | | | | |
| MCF7 | 1.55 | 3.18 | 2.30 | 2.47 | 1.27 | 0.31 | 0.44 | 0.47 | 1.74 | 0.47 |
| MDA-MB-231/ATCC | 3.36 | 5.25 | 3.87 | 3.86 | 3.35 | 2.17 | 5.48 | 4.19 | 13.8 | 1.66 |
| HS 578T | 4.16 | 4.25 | 4.67 | 6.14 | 4.00 | 3.41 | 3.39 | na | 5.96 | 2.01 |
| BT-549 | 2.78 | 4.57 | 2.52 | 9.32 | 1.45 | 1.93 | 2.59 | 1.52 | 12.3 | 1.89 |
| TD-47D | 2.70 | 3.60 | 3.09 | 4.24 | 1.92 | 2.19 | 3.84 | 3.08 | 6.65 | 1.11 |
| Melanoma | | | | | | | | | | |
| LOX IMVI | 1.88 | 2.44 | 1.63 | 1.85 | 1.57 | 0.48 | 0.72 | 1.23 | 1.72 | 0.85 |
| MALME-3M | 2.67 | 4.42 | 3.06 | 6.21 | 1.83 | 1.31 | 1.79 | 1.80 | 18.1 | 2.08 |
| M14 | 2.61 | 5.14 | 2.86 | 4.53 | 2.01 | 1.35 | 1.85 | 2.12 | 4.36 | 1.49 |
| MDA-MB-435 | 2.14 | 3.35 | 2.25 | 3.12 | 2.06 | 1.20 | 1.86 | 2.11 | 3.63 | 1.71 |
| SK-MEL-2 | 3.65 | 5.54 | 3.66 | 8.26 | 2.07 | 2.06 | 2.63 | 3.02 | 3.44 | 2.31 |
| SK-MEL-28 | 1.85 | 2.03 | 2.06 | 5.63 | 3.64 | 1.74 | 2.03 | 1.61 | 10.9 | 3.79 |
| SK-MEL-5 | 1.59 | 2.63 | 1.80 | 3.18 | 1.53 | 1.40 | 2.03 | 2.76 | 8.70 | 1.16 |
| UACC-257 | 6.81 | 13.3 | 8.69 | 7.68 | 4.07 | 1.52 | 3.04 | 2.22 | 17.4 | 4.13 |
| UACC-62 | 2.01 | 3.96 | 2.74 | 3.65 | 1.85 | 1.52 | 2.06 | 1.87 | 8.88 | 1.80 |

TABLE 2

The mean graph midpoint values (MG_MID) of Logic$_{10}$ GI$_{50}$ (log values of concentration in mol/L causing 50% inhibition of net cell growth) values for compounds 3a, 3b 3f, 4a, 4f, 5a, 5b, 5d, 5f and 12b in fifty three cancer cell lines.

| Cancer cell lines Log$_{10}$ GI$_{50}$ | 3a | 3b | 3f | 4a | 4f | 5a | 5b | 5d | 5f | 12b |
|---|---|---|---|---|---|---|---|---|---|---|
| Leukemia | 5.73 | 5.75 | 5.86 | 5.64 | 6.10 | 6.25 | 5.96 | 6.42 | 5.42 | 5.81 |
| Non-small cell lung | 5.59 | 5.33 | 5.45 | 5.16 | 5.63 | 5.51 | 5.30 | 4.86 | 4.72 | 5.76 |
| Colon | 5.67 | 5.54 | 5.69 | 5.56 | 5.63 | 6.08 | 5.95 | 5.72 | 5.53 | 5.99 |
| CNS | 5.59 | 5.33 | 5.50 | 5.24 | 5.84 | 5.73 | 5.54 | 5.51 | 5.08 | 5.83 |
| Melanoma | 5.59 | 5.39 | 5.55 | 5.35 | 5.66 | 5.88 | 5.72 | 5.69 | 5.17 | 5.71 |
| Ovarian | 5.49 | 5.41 | 5.56 | 5.33 | 5.69 | 5.76 | 5.58 | 5.53 | 5.26 | 5.74 |
| Renal | 5.62 | 5.33 | 5.53 | 5.38 | 5.75 | 5.72 | 5.60 | 5.58 | 5.15 | 5.05 |
| Prostate | 5.60 | 5.52 | 5.71 | 5.55 | nt | 5.49 | 5.21 | 5.58 | nt | 5.73 |
| Breast | 5.55 | 5.38 | 5.49 | 5.32 | 5.66 | 5.80 | 5.61 | 5.40 | 5.18 | 5.89 |

TABLE 3

The mean graph midpoint values (MG_MID) of Log$_{10}$ LC$_{50}$ values (log value of the concentration of compounds leading to 50% net cell death) for compounds 3a, 3b 3f, 4a, 4f, 5a, 5b, 5d, f and 12b in fifty three cancer cell lines.

| Cancer cell lines Log$_{10}$ LC$_{50}$ | 3a | 3b | 3f | 4a | 4f | 5a | 5b | 5d | 5f | 12b |
|---|---|---|---|---|---|---|---|---|---|---|
| Leukemia | 4.18 | 4.42 | 4.26 | 4.00 | 4.06 | 4.00 | 4.00 | 4.00 | 4.00 | 4.00 |
| Non-small cell lung | 4.38 | 4.00 | 4.07 | 3.80 | 4.24 | 4.49 | 4.82 | 3.94 | 4.06 | 4.70 |

TABLE 3-continued

The mean graph midpoint values (MG_MID) of Log$_{10}$ LC$_{50}$ values (log value of the concentration of compounds leading to 50% net cell death) for compounds 3a, 3b 3f, 4a, 4f, 5a, 5b, 5d, f and 12b in fifty three cancer cell lines.

| Cancer cell lines Log$_{10}$ LC$_{50}$ | 3a | 3b | 3f | 4a | 4f | 5a | 5b | 5d | 5f | 12b |
|---|---|---|---|---|---|---|---|---|---|---|
| Colon | 4.68 | 4.33 | 4.53 | 4.55 | 4.68 | 5.23 | 5.13 | 4.19 | 4.76 | 5.08 |
| CNS | 4.62 | 4.06 | 4.29 | 4.60 | 4.87 | 5.13 | 4.55 | 4.29 | 4.24 | 5.04 |
| Melanoma | 4.06 | 4.13 | 4.32 | 4.35 | 4.55 | 5.02 | 4.58 | 4.67 | 4.24 | 4.62 |
| Ovarian | 4.93 | 4.00 | 4.36 | 4.33 | 4.33 | 4.37 | 4.41 | 4.12 | 4.22 | 4.59 |
| Renal | 4.46 | 4.02 | 4.20 | 4.47 | 4.56 | 4.77 | 4.46 | 4.56 | 3.73 | 4.99 |
| Prostate | 4.00 | 4.00 | 4.18 | 4.31 | nt | 4.00 | 4.00 | 4.00 | nt | 4.10 |
| Breast | 4.27 | 4.00 | 4.02 | 4.14 | 4.20 | 4.42 | 4.91 | 4.34 | 4.11 | 4.50 |

TABLE 4

The mean graph midpoint values (MG_MID) of log$_{10}$TGI (log value of concentration of the compound resulting in total inhibition of net cell growth) for compounds 3a, 3b 3f, 4a, 4f, 5a, 5b, 5d, 5f and 12b in fifty three cancer cell lines.

| Cancer cell lines Log10 TGI | 3a | 3b | 3f | 4a | 4f | 5a | 5b | 5d | 5f | 12b |
|---|---|---|---|---|---|---|---|---|---|---|
| Leukemia | 5.19 | 5.14 | 5.29 | 4.59 | 5.38 | 4.00 | 4.00 | 5.07 | 4.00 | 5.23 |
| Non-small cell lung | 5.11 | 4.31 | 4.76 | 4.10 | 5.04 | 4.89 | 4.66 | 4.33 | 4.28 | 5.22 |
| Colon | 5.14 | 4.84 | 5.09 | 4.85 | 5.24 | 5.63 | 5.58 | 5.44 | 5.15 | 5.59 |
| CNS | 5.11 | 4.47 | 4.99 | 4.91 | 5.47 | 5.30 | 5.01 | 4.91 | 4.50 | 5.44 |
| Melanoma | 5.17 | 4.61 | 4.94 | 4.75 | 5.19 | 5.49 | 5.25 | 5.27 | 4.56 | 5.25 |
| Ovarian | 4.74 | 4.53 | 4.81 | 4.74 | 4.97 | 5.21 | 4.83 | 4.70 | 4.62 | 5.13 |
| Renal | 5.17 | 4.46 | 4.73 | 4.84 | 5.29 | 5.29 | 5.12 | 5.10 | 4.55 | 5.44 |
| Prostate | 5.13 | 4.80 | 5.20 | 4.90 | nt | 4.68 | 4.41 | 4.73 | nt | 5.10 |
| Breast | 4.95 | 4.30 | 4.63 | 4.70 | 5.03 | 5.23 | 4.86 | 4.85 | 4.38 | 5.39 |

TABLE 5 pGI$_{50}$ valves (-log of molar concentration of the compound require to cause 50% inhibition of net cell growth) of compounds 3a, 3b 3f, 4a, 4f, 5a, 5b, 5d, 5f and 12b in fifty three cancer cell lines.

| Compound | 3a | 3b | 3f | 4a | 4f | 5a | 5b | 5d | 5f | 12b |
|---|---|---|---|---|---|---|---|---|---|---|
| Panell cell line Leukemia | | | | | | | | | | |
| RPMI-8226 | 5.78 | 5.87 | 5.88 | 5.67 | 5.81 | 6.21 | 6.04 | 6.64 | 5.41 | 5.78 |
| K-562 | 5.69 | 5.63 | 5.85 | 5.47 | 6.40 | 6.30 | 5.90 | 6.23 | 5.43 | 5.84 |
| Non-small cell lung cancer | | | | | | | | | | |
| A549/ATCC | 5.41 | 5.38 | 5.17 | 5.41 | 5.45 | 5.39 | 4.93 | 5.52 | 4.07 | 5.47 |
| EKVX | 5.41 | 4.87 | 5.02 | 4.81 | 5.62 | 5.64 | 5.38 | 5.02 | 4.62 | 5.58 |
| HOP-62 | 5.83 | 5.29 | 5.55 | 5.16 | 5.63 | 5.39 | 5.23 | 5.51 | 4.63 | 5.65 |
| HOP-92 | 5.64 | 5.53 | 5.90 | 5.30 | 5.80 | 4.97 | 4.83 | nt | na | 6.29 |
| NCI-H226 | 5.59 | 5.39 | 5.56 | 4.61 | 5.64 | 4.84 | 4.45 | 4.84 | na | 5.61 |
| NCI-H23 | 5.69 | 5.55 | 5.50 | 5.47 | 5.56 | 5.84 | 5.79 | 5.70 | 5.45 | 5.82 |
| NCI-H322M | 5.47 | 5.09 | 5.34 | 4.97 | 5.60 | 5.69 | 5.58 | 5.44 | 4.89 | 5.78 |
| NCI-H460 | 5.71 | 5.49 | 5.41 | 5.60 | 5.62 | 5.85 | 5.81 | 5.76 | 5.43 | 5.78 |
| NCI-H522 | 5.63 | 5.46 | 5.63 | nt | 5.78 | 6.02 | 5.73 | 5.98 | 5.39 | 5.89 |
| Colon cancer | | | | | | | | | | |
| COLO205 | 5.66 | 5.18 | 5.47 | 5.70 | 5.64 | 5.82 | 5.74 | 5.82 | 5.13 | 5.68 |
| HCC-2998 | 5.82 | 5.63 | 5.73 | 5.39 | 4.86 | 5.90 | 5.79 | 5.72 | 5.61 | 5.67 |
| HCT-116 | 5.85 | 5.71 | 5.84 | 5.52 | 5.91 | 6.48 | 6.43 | 6.13 | 5.86 | 6.40 |
| HCT-15 | 5.56 | 5.50 | 5.74 | 5.51 | 5.63 | 5.95 | 5.86 | 5.72 | 5.41 | 5.81 |
| HT29 | 5.42 | 5.42 | 5.53 | 5.48 | 5.72 | 6.18 | 5.89 | 5.77 | 5.70 | 5.81 |
| KM12 | 5.79 | 5.75 | 5.83 | 5.74 | 5.87 | 5.86 | 5.85 | 5.95 | 5.26 | 5.92 |
| SW-620 | 5.64 | 5.60 | 5.70 | 5.62 | 5.79 | 6.41 | 6.35 | 5.99 | 5.76 | 6.66 |
| CNS cancer | | | | | | | | | | |
| SF-268 | 5.68 | 5.47 | 5.60 | 5.34 | 5.75 | 5.72 | 5.49 | 5.66 | 5.29 | 5.76 |
| SF-295 | 5.52 | 4.86 | 4.98 | 4.74 | 5.75 | 5.72 | 5.31 | 5.30 | 4.61 | 5.84 |
| SF-539 | 5.72 | 5.65 | 5.75 | 5.70 | 5.77 | 5.77 | 5.70 | 5.51 | 5.46 | 5.81 |
| SNB-19 | 5.53 | 5.23 | 5.50 | 4.96 | 5.72 | 5.63 | 5.36 | 5.39 | 4.79 | 5.88 |
| SNB-75 | 5.41 | 5.33 | 5.56 | 4.92 | 5.84 | 5.35 | 5.34 | 5.29 | 4.69 | 5.73 |
| U251 | 5.68 | 5.46 | 5.65 | 5.79 | 6.24 | 6.20 | 6.06 | 5.91 | 5.67 | 5.96 |

TABLE 5-continued pGI$_{50}$ valves (-log of molar concentration of the compound require to cause 50% inhibition of net cell growth) of compounds 3a, 3b 3f, 4a, 4f, 5a, 5b, 5d, 5f and 12b in fifty three cancer cell lines.

| Compound | 3a | 3b | 3f | 4a | 4f | 5a | 5b | 5d | 5f | 12b |
|---|---|---|---|---|---|---|---|---|---|---|
| Renal cancer | | | | | | | | | | |
| 786-0 | 5.87 | 5.34 | 5.68 | 5.53 | 5.80 | 5.86 | 5.79 | 5.80 | 5.67 | 5.76 |
| A498 | 5.77 | 5.43 | 5.55 | 4.84 | 5.43 | 5.58 | 5.38 | 4.69 | 4.52 | nt |
| ACHN | 5.60 | 5.47 | 5.66 | 5.56 | 5.74 | 5.80 | 5.74 | 5.76 | 5.14 | 5.80 |
| CAKI-1 | 5.66 | 5.30 | 5.58 | 4.88 | 5.76 | 5.76 | 5.52 | 5.54 | 4.81 | 5.84 |
| RXF-393 | 5.64 | 5.23 | 5.19 | 5.72 | 5.82 | 5.77 | 5.72 | 5.79 | 5.49 | 5.85 |
| SN 12C | 5.48 | 5.39 | 5.54 | 5.50 | 5.71 | 5.68 | 5.56 | 5.56 | 5.29 | 5.84 |
| TK-10 | 5.28 | 5.22 | 5.33 | nt | 5.55 | 5.52 | 5.52 | 5.52 | 5.19 | 5.46 |
| UO-31 | 5.66 | 5.28 | 5.78 | 5.67 | 6.26 | 5.82 | 5.72 | 6.02 | 5.15 | 5.90 |
| Prostate cancer | | | | | | | | | | |
| PC-3 | 5.60 | 5.52 | 5.71 | 5.55 | nt | 5.49 | 5.21 | 5.58 | nt | 5.73 |
| ovarian | | | | | | | | | | |
| OVCAR-3 | 5.64 | 5.57 | 5.81 | 5.51 | 5.81 | 5.91 | 5.75 | 5.83 | 5.61 | 5.88 |
| OVCAR-4 | 5.28 | 5.22 | 5.33 | 5.28 | 5.66 | 5.73 | 5.45 | 5.42 | 4.94 | 5.77 |
| OVCAR-5 | 5.69 | 5.47 | 5.70 | 5.26 | 5.66 | 5.73 | 5.58 | 5.36 | 5.51 | 5.72 |
| OVCAR-8 | 5.39 | 5.30 | 5.38 | 5.55 | 6.00 | 5.79 | 5.60 | 5.63 | 5.41 | 5.63 |
| NCI/ADR-RES | 5.53 | 5.59 | 5.64 | 5.43 | 5.66 | 5.96 | 5.77 | 5.68 | 5.63 | 5.81 |
| SK-OV-3 | 5.42 | 5.32 | 5.50 | 4.95 | 5.38 | 5.49 | 5.34 | 5.29 | 4.50 | 5.67 |
| Breast cancer | | | | | | | | | | |
| MCF7 | 5.81 | 5.50 | 5.64 | 5.61 | 5.89 | 6.51 | 6.36 | 6.33 | 5.76 | 6.33 |
| MDA-MB-231/ATCC | 5.47 | 5.28 | 5.41 | 5.41 | 5.47 | 5.66 | 5.26 | 5.38 | 4.86 | 5.78 |
| HS 578T | 5.38 | 5.37 | 5.33 | 5.21 | 5.40 | 5.47 | 5.47 | na | 5.22 | 5.70 |
| BT-549 | 5.56 | 5.34 | 5.60 | 5.03 | 5.84 | 5.71 | 5.59 | 5.82 | 4.91 | 5.72 |
| TD-47D | 5.57 | 5.44 | 5.51 | 5.37 | 5.72 | 5.66 | 5.42 | 5.51 | 5.18 | 5.95 |
| Melanoma | | | | | | | | | | |
| LOX IMVI | 5.73 | 5.61 | 5.79 | 5.73 | 5.80 | 6.32 | 6.14 | 5.91 | 5.76 | 6.07 |
| MALME-3M | 5.57 | 5.35 | 5.51 | 5.21 | 5.74 | 5.88 | 5.75 | 5.74 | 4.74 | 5.68 |
| M14 | 5.58 | 5.29 | 5.54 | 5.34 | 5.70 | 5.87 | 5.73 | 5.67 | 5.36 | 5.83 |
| MDA-MB-435 | 5.67 | 5.47 | 5.65 | 5.51 | 5.69 | 5.92 | 5.73 | 5.68 | 5.44 | 5.77 |
| SK-MEL-2 | 5.44 | 5.26 | 5.44 | 5.08 | 5.68 | 5.69 | 5.58 | 5.52 | 5.46 | 5.64 |
| SK-MEL-28 | 5.73 | 5.69 | 5.69 | 5.25 | 5.44 | 5.76 | 5.69 | 5.79 | 4.96 | 5.42 |
| SK-MEL-5 | 5.80 | 5.58 | 5.74 | 5.50 | 5.82 | 5.85 | 5.69 | 5.56 | 5.06 | 5.94 |
| UACC-257 | 5.17 | 4.88 | 5.06 | 5.11 | 5.39 | 5.82 | 5.52 | 5.65 | 4.76 | 5.38 |
| UACC-62 | 5.70 | 5.40 | 5.56 | 5.44 | 5.73 | 5.82 | 5.69 | 5.73 | 5.05 | 5.74 |

TABLE 6

Comparative activity of the compounds of the present invention (chalcone linked imidazolone) over imidazolone and chalcone.

| SNo | A(μm) | B(μm) | C(μm) | D(μm) | 5a(μm) | 5b(μm) |
|---|---|---|---|---|---|---|
| A549 | 186 | 346 | 930 | 262 | 4.03 | 11.8 |
| HT29 | 147 | 443 | 313 | 308 | 0.66 | 1.28 |

A = (E)-1-(3-aminophenyl)-3-(4-hydroxy-3-methoxyphenyl)-2-propen-1-one (Chalcone)
B = (E)-1-(3-aminophenyl)-3-(3-hydroxyphenyl)-2-propen-1-one (Chalcone)
C = (E)-1-(3-aminophenyl)-3-(3,4,5-trimethoxyphenyl)-2-propen-1-one (Chalcone)
D = 1-(3-acetylphenyl)-4-(4-methoxyphenyl)-2,3-dihydro-1H-2-imidazolone (imidazolone)
5a and 5b = Representative imidazolone linked chalcones of the present invention From the Table it is observed that, imidazolone linked chalcones of the present invention (5a and 5b) have exhibited better anticancer activity as compared to basic individual subunits i.e. chalcones (A, B, C) and imidazolones (D).

Significance of the Work Carried Out

The chalcone linked imidazolones exhibited significant cytotoxic activity against fifty three human cancer cell lines.

Advantages of the Invention

1. The present invention provides chalcone linked imidazolones compounds of general formula A.
2. It also provides a process for the preparation of chalcone linked imidazolones of general formula A.

We claim:

1. A chalcone linked imidazolone compound of formula A

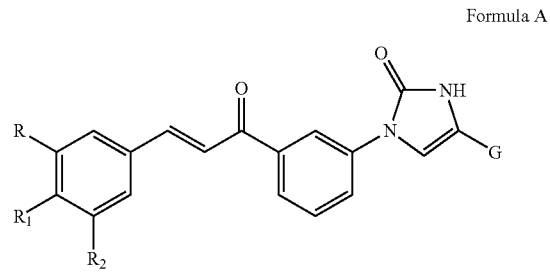

Formula A

Wherein

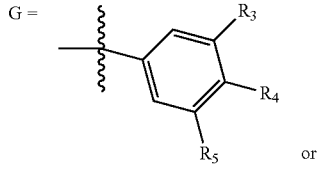

or

-continued

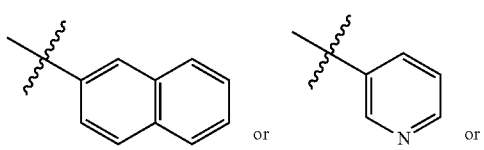

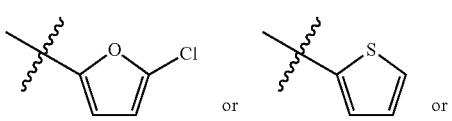

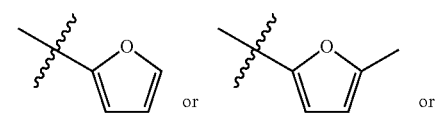

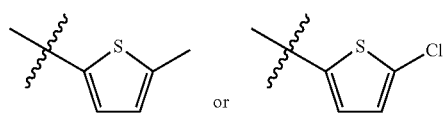

R = H, OMe
R₁ = H, Cl, F, OH, OMe
R₂ = H, OH, OMe
R₃ = H, OMe, CH₃
R₄ = H, Cl, F, OH, OMe, CH₃
R₅ = H, OMe, CH₃

I.

Formula 3a-j to 11a-j

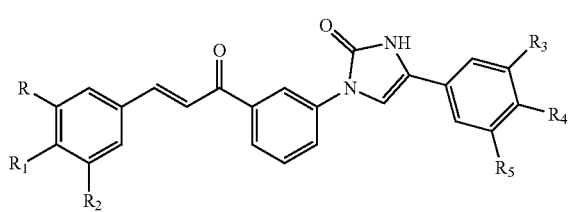

R = H, OMe
R₁ = H, Cl, F, OH, OMe
R₂ = H, OH, OMe
R₃ = H, OMe, CH₃
R₄ = H, Cl, F, OH, OMe, CH₃
R₅ = H, OMe, CH₃

Formula 12a-i

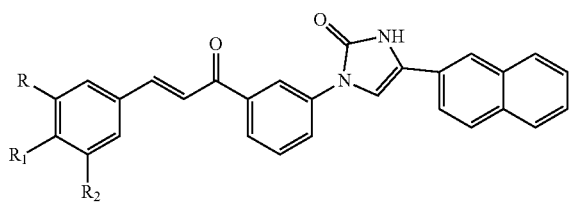

R = H, OMe
R₁ = H, Cl, F, OH, OMe
R₂ = H, OH, OMe

Formula 13a-i

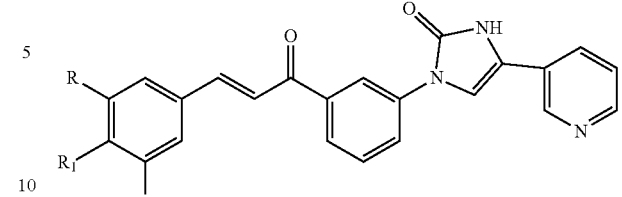

R = H, OMe
R₁ = H, Cl, F, OH, OMe
R₂ = H, OH, OMe

Formula 14a-i to 19a-i

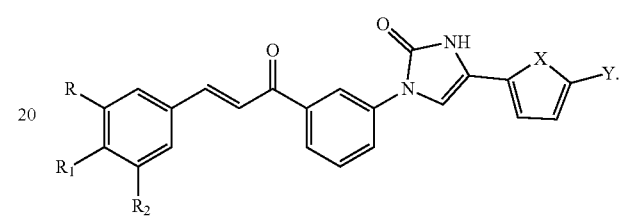

R = H, OMe
R₁ = H, Cl, F, OH, OMe
R₂ = H, OH, OMe
X = O, S
Y = H, Cl, CH₃

2. The chalcone linked imidazolone compound as claimed in claim 1, wherein the chalcone linked imidazolone compound is selected from the group consisting of:

(3a) 1-3-[(E)-3-(4-hydroxy-3-methoxyphenyl)-2-propenoyl]phenyl-4-phenyl-2,3-dihydro-1H-2-imidazolone;

(3b) 1-3-[(E)-3-(4-hydroxy-3-methoxyphenyl)-2-propenoyl]phenyl-4-(4-methoxyphenyl)-2,3-dihydro-1H-2-imidazolone;

(3c) 4-(3,4-dimethoxyphenyl)-1-3-[(E)-3-(4-hydroxy-3-methoxyphenyl)-2-propenoyl]phenyl-2,3-dihydro-1H-2-imidazolone;

(3d) 1-3-[(E)-3-(4-hydroxy-3-methoxyphenyl)-2-propenoyl]phenyl-4-(3,4,5-trimethoxyphenyl)-2,3-dihydro-1H-2-imidazolone;

(3e) 4-(4-fluorophenyl)-1-3-[(E)-3-(4-hydroxy-3-methoxyphenyl)-2-propenoyl]phenyl-2,3-dihydro-1H-2-imidazolone;

(3f) 4-(4-chlorophenyl)-1-3-[(E)-3-(4-hydroxy-3-methoxyphenyl)-2-propenoyl]phenyl-2,3-dihydro-1H-2-imidazolone;

(3g) 1-3-[(E)-3-(4-hydroxy-3-methoxyphenyl)-2-propenoyl]phenyl-4-(4-methylphenyl)-2,3-dihydro-1H-2-imidazolone;

(3h) 4-(3,4-dimethylphenyl)-1-3-[(E)-3-(4-hydroxy-3-methoxyphenyl)-2-propenoyl]phenyl-2,3-dihydro-1H-2-imidazolone;

(3i) 1-3-[(E)-3-(4-hydroxy-3-methoxyphenyl)-2-propenoyl]phenyl-4-(3,4,5-trimethylphenyl)-2,3-dihydro-1H-2-imidazolone;

(3j) 1-3-[(E)-3-(4-hydroxy-3-methoxyphenyl)-2-propenoyl]phenyl-4-(4-hydroxyphenyl)-2,3-dihydro-1H-2-imidazolone;

(4a) 1-3-[(E)-3-(3-hydroxyphenyl)-2-propenoyl]phenyl-4-phenyl-2,3-dihydro-1H-2-imidazolone;

(4b) 1-3-[(E)-3-(3-hydroxyphenyl)-2-propenoyl]phenyl-4-(4-methoxyphenyl)-2,3-dihydro-1H-2-imidazolone;

(4c) 4-(3,4-dimethoxyphenyl)-1-3-[(E)-3-(3-hydroxyphenyl)-2-propenoyl]phenyl-2,3-dihydro-1H-2-imidazolone;
(4d) 1-3-[(E)-3-(3-hydroxyphenyl)-2-propenoyl]phenyl-4-(3,4,5-trimethoxyphenyl)-2,3-dihydro-1H-2-imidazolone;
(4e) 4-(4-fluorophenyl)-1-3-[(E)-3-(3-hydroxyphenyl)-2-propenoyl]phenyl-2,3-dihydro-1H-2-imidazolone;
(4f) 4-(4-chlorophenyl)-1-3-[(E)-3-(3-hydroxyphenyl)-2-propenoyl]phenyl-2,3-dihydro-1H-2-imidazolone;
(4g) 1-3-[(E)-3-(3-hydroxyphenyl)-2-propenoyl]phenyl-4-(4-methyl phenyl)-2,3-dihydro-1H-2-imidazolone;
(4h) 4-(3,4-dimethylphenyl)-1-3-[(E)-3-(3-hydroxyphenyl)-2-propenoyl]phenyl-2,3-dihydro-1H-2-imidazolone;
(4i) 1-3-[(E)-3-(3-hydroxyphenyl)-2-propenoyl]phenyl-4-(3,4,5-trimethylphenyl)-2,3-dihydro-1H-2-imidazolone;
(4j) 4-(4-hydroxyphenyl)-1-3-[(E)-3-(3-hydroxyphenyl)-2-propenoyl]phenyl-2,3-dihydro-1H-2-imidazolone;
(5a) 4-phenyl-1-3-[(E)-3-(3,4,5-trimethoxyphenyl)-2-propenoyl]phenyl-2,3-dihydro-1H-2-imidazolone;
(5b) 4-(4-methoxyphenyl)-1-3-[(E)-3-(3,4,5-trimethoxyphenyl)-2-propenoyl]phenyl-2,3-dihydro-1H-2-imidazolone;
(5c) 4-(3,4-dimethoxyphenyl)-1-3-[(E)-3-(3,4,5-trimethoxyphenyl)-2-propenoyl]phenyl-2,3-dihydro-1H-2-imidazolone;
(5d) 4-(3,4,5-trimethoxyphenyl)-1-3-[(E)-3-(3,4,5-trimethoxyphenyl)-2-propenoyl]phenyl-2,3-dihydro-1H-2-imidazolone;
(5e) 4-(4-fluorophenyl)-1-3-[(E)-3-(3,4,5-trimethoxyphenyl)-2-propenoyl]phenyl-2,3-dihydro-1H-2-imidazolone;
(5f) 4-(4-chlorophenyl)-1-3-[(E)-3-(3,4,5-trimethoxyphenyl)-2-propenoyl]phenyl-2,3-dihydro-1H-2-imidazolone;
(5g) 4-(4-methylphenyl)-1-3-[(E)-3-(3,4,5-trimethoxyphenyl)-2-propenoyl]phenyl-2,3-dihydro-1H-2-imidazolone;
(5h) 4-(3,4-dimethylphenyl)-1-3-[(E)-3-(3,4,5-trimethoxyphenyl)-2-propenoyl]phenyl-2,3-dihydro-1H-2-imidazolone;
(5i) 1-3-[(E)-3-(3,4,5-trimethoxyphenyl)-2-propenoyl]phenyl-4-(3,4,5-trimethylphenyl)-2,3-dihydro-1H-2-imidazolone;
(5j) 4-(4-hydroxyphenyl)-1-3-[(E)-3-(3,4,5-trimethoxyphenyl)-2-propenoyl]phenyl-2,3-dihydro-1H-2-imidazolone;
(6a) 1-3-[(E)-3-(3,4-dimethoxyphenyl)-2-propenoyl]phenyl-4-phenyl-2,3-dihydro-1H-2-imidazolone;
(6b) 1-3-[(E)-3-(3,4-dimethoxyphenyl)-2-propenoyl]phenyl-4-(4-methoxyphenyl)-2,3-dihydro-1H-2-imidazolone;
(6c) 4-(3,4-dimethoxyphenyl)-1-3-[(E)-3-(3,4-dimethoxyphenyl)-2-propenoyl]phenyl-2,3-dihydro-1H-2-imidazolone;
(6d) 1-3-[(E)-3-(3,4-dimethoxyphenyl)-2-propenoyl]phenyl-4-(3,4,5-trimethoxyphenyl)-2,3-dihydro-1H-2-imidazolone;
(6e) 1-3-[(E)-3-(3,4-dimethoxyphenyl)-2-propenoyl]phenyl-4-(4-fluorophenyl)-2,3-dihydro-1H-2-imidazolone;
(6f) 4-(4-chlorophenyl)-1-3-[(E)-3-(3,4-dimethoxyphenyl)-2-propenoyl]phenyl-2,3-dihydro-1H-2-imidazolone;
(6g) 1-3-[(E)-3-(3,4-dimethoxyphenyl)-2-propenoyl]phenyl-4-(4-methylphenyl)-2,3-dihydro-1H-2-imidazolone;
(6h) 1-3-[(E)-3-(3,4-dimethoxyphenyl)-2-propenoyl]phenyl-4-(3,4-dimethylphenyl)-2,3-dihydro-1H-2-imidazolone;
(6i) 1-3-[(E)-3-(3,4-dimethoxyphenyl)-2-propenoyl]phenyl-4-(3,4,5-trimethylphenyl)-2,3-dihydro-1H-2-imidazolone;
(6j) 1-3-[(E)-3-(3,4-dimethoxyphenyl)-2-propenoyl]phenyl-4-(4-hydroxyphenyl)-2,3-dihydro-1H-2-imidazolone;
(7a) 1-3-[(E)-3-(4-methoxyphenyl)-2-propenoyl]phenyl-4-phenyl-2,3-dihydro-1H-2-imidazolone;
(7b) 4-(4-methoxyphenyl)-1-3-[(E)-3-(4-methoxyphenyl)-2-propenoyl]phenyl-2,3-dihydro-1H-2-imidazolone;
(7c) 4-(3,4-dimethoxyphenyl)-1-3-[(E)-3-(4-methoxyphenyl)-2-propenoyl]phenyl-2,3-dihydro-1H-2-imidazolone;
(7d) 1-3-[(E)-3-(4-methoxyphenyl)-2-propenoyl]phenyl-4-(3,4,5-trimethoxyphenyl)-2,3-dihydro-1H-2-imidazolone;
(7e) 4-(4-fluorophenyl)-1-3-[(E)-3-(4-methoxyphenyl)-2-propenoyl]phenyl-2,3-dihydro-1H-2-imidazolone;
(7f) 4-(4-chlorophenyl)-1-3-[(E)-3-(4-methoxyphenyl)-2-propenoyl]phenyl-2,3-dihydro-1H-2-imidazolone;
(7g) 1-3-[(E)-3-(4-methoxyphenyl)-2-propenoyl]phenyl-4-(4-methylphenyl)-2,3-dihydro-1H-2-imidazolone;
(7h) 4-(3,4-dimethylphenyl)-1-3-[(E)-3-(4-methoxyphenyl)-2-propenoyl]phenyl-2,3-dihydro-1H-2-imidazolone;
(7i) 1-3-[(E)-3-(4-methoxyphenyl)-2-propenoyl]phenyl-4-(3,4,5-trimethylphenyl)-2,3-dihydro-1H-2-imidazolone;
(7j) 4-(4-hydroxyphenyl)-1-3-[(E)-3-(4-methoxyphenyl)-2-propenoyl]phenyl-2,3-dihydro-1H-2-imidazolone;
(8a) 4-phenyl-1-3-[(E)-3-phenyl-2-propenoyl]phenyl-2,3-dihydro-1H-2-imidazolone;
(8b) 4-(4-methoxyphenyl)-1-3-[(E)-3-phenyl-2-propenoyl]phenyl-2,3-dihydro-1H-2-imidazolone;
(8c) 4-(3,4-dimethoxyphenyl)-1-3-[(E)-3-phenyl-2-propenoyl]phenyl-2,3-dihydro-1H-2-imidazolone;
(8d) 1-3-[(E)-3-phenyl-2-propenoyl]phenyl-4-(3,4,5-trimethoxyphenyl)-2,3-dihydro-1H-2-imidazolone;
(8e) 4-(4-fluorophenyl)-1-3-[(E)-3-phenyl-2-propenoyl]phenyl-2,3-dihydro-1H-2-imidazolone;
(8f) 4-(4-chlorophenyl)-1-3-[(E)-3-phenyl-2-propenoyl]phenyl-2,3-dihydro-1H-2-imidazolone;
(8g) 4-(4-methylphenyl)-1-3-[(E)-3-phenyl-2-propenoyl]phenyl-2,3-dihydro-1H-2-imidazolone;
(8h) 4-(3,4-dimethylphenyl)-1-3-[(E)-3-phenyl-2-propenoyl]phenyl-2,3-dihydro-1H-2-imidazolone;
(8i) 1-3-[(E)-3-phenyl-2-propenoyl]phenyl-4-(3,4,5-trimethylphenyl)-2,3-dihydro-1H-2-imidazolone;
(8j) 4-(4-hydroxyphenyl)-1-3-[(E)-3-phenyl-2-propenoyl]phenyl-2,3-dihydro-1H-2-imidazolone;
(9a) 1-3-[(E)-3-(4-fluorophenyl)-2-propenoyl]phenyl-4-phenyl-2,3-dihydro-1H-2-imidazolone;
(9b) 1-3-[(E)-3-(4-fluorophenyl)-2-propenoyl]phenyl-4-(4-methoxyphenyl)-2,3-dihydro-1H-2-imidazolone;
(9c) 4-(3,4-dimethoxyphenyl)-1-3-[(E)-3-(4-fluorophenyl)-2-propenoyl]phenyl-2,3-dihydro-1H-2-imidazolone;
(9d) 1-3-[(E)-3-(4-fluorophenyl)-2-propenoyl]phenyl-4-(3,4,5-trimethoxyphenyl)-2,3-dihydro-1H-2-imidazolone;

(9e) 4-(4-fluorophenyl)-1-3-[(E)-3-(4-fluorophenyl)-2-propenoyl]phenyl-2,3-dihydro-1H-2-imidazolone;
(9f) 4-(4-chlorophenyl)-1-3-[(E)-3-(4-fluorophenyl)-2-propenoyl]phenyl-2,3-dihydro-1H-2-imidazolone;
(9g) 1-3-[(E)-3-(4-fluorophenyl)-2-propenoyl]phenyl-4-(4-methylphenyl)-2,3-dihydro-1H-2-imidazolone;
(9f) 4-(3,4-dimethylphenyl)-1-3-[(E)-3-(4-fluorophenyl)-2-propenoyl]phenyl-2,3-dihydro-1H-2-imidazolone;
(9i) 1-3-[(E)-3-(4-fluorophenyl)-2-propenoyl]phenyl-4-(3,4,5-trimethylphenyl)-2,3-dihydro-1H-2-imidazolone;
(9j) 1-3-[(E)-3-(4-fluorophenyl)-2-propenoyl]phenyl-4-(4-hydroxyphenyl)-2,3-dihydro-1H-2-imidazolone;
(10a) 1-3-[(E)-3-(4-chlorophenyl)-2-propenoyl]phenyl-4-phenyl-2,3-dihydro-1H-2-imidazolone;
(10b) 1-3-[(E)-3-(4-chlorophenyl)-2-propenoyl]phenyl-4-(4-methoxyphenyl)-2,3-dihydro-1H-2-imidazolone;
(10c) 1-3-[(E)-3-(4-chlorophenyl)-2-propenoyl]phenyl-4-(3,4-dimethoxyphenyl)-2,3-dihydro-1H-2-imidazolone;
(10d) 1-3-[(E)-3-(4-chlorophenyl)-2-propenoyl]phenyl-4-(3,4,5-trimethoxyphenyl)-2,3-dihydro-1H-2-imidazolone;
(10e) 1-3-[(E)-3-(4-chlorophenyl)-2-propenoyl]phenyl-4-(4-fluorophenyl)-2,3-dihydro-1H-2-imidazolone;
(10f) 4-(4-chlorophenyl)-1-3-[(E)-3-(4-chlorophenyl)-2-propenoyl]phenyl-2,3-dihydro-1H-2-imidazolone;
(10g) 1-3-[(E)-3-(4-chlorophenyl)-2-propenoyl]phenyl-4-(4-methylphenyl)-2,3-dihydro-1H-2-imidazolone;
(10h) 1-3-[(E)-3-(4-chlorophenyl)-2-propenoyl]phenyl-4-(3,4-dimethylphenyl)-2,3-dihydro-1H-2-imidazolone;
(10i) 1-3-[(E)-3-(4-chlorophenyl)-2-propenoyl]phenyl-4-(3,4,5-trimethylphenyl)-2,3-dihydro-1H-2-imidazolone;
(10j) 1-3-[(E)-3-(4-chlorophenyl)-2-propenoyl]phenyl-4-(4-hydroxyphenyl)-2,3-dihydro-1H-2-imidazolone;
(11a) 1-3-[(E)-3-(4-hydroxy-3,5-dimethoxyphenyl)-2-propenoyl]phenyl-4-phenyl-2,3-dihydro-1H-2-imidazolone;
(11b) 1-3-[(E)-3-(4-hydroxy-3,5-dimethoxyphenyl)-2-propenoyl]phenyl-4-(4-methoxyphenyl)-2,3-dihydro-1H-2-imidazolone;
(11c) 4-(3,4-dimethoxyphenyl)-1-3-[(E)-3-(4-hydroxy-3,5-dimethoxyphenyl)-2-propenoyl]phenyl-2,3-dihydro-1H-2-imidazolone;
(11d) 1-3-[(E)-3-(4-hydroxy-3,5-dimethoxyphenyl)-2-propenoyl]phenyl-4-(3,4,5-trimethoxyphenyl)-2,3-dihydro-1H-2-imidazolone;
(11e) 4-(4-fluorophenyl)-1-3-[(E)-3-(4-hydroxy-3,5-dimethoxyphenyl)-2-propenoyl]phenyl-2,3-dihydro-1H-2-imidazolone;
(11f) 4-(4-chlorophenyl)-1-3-[(E)-3-(4-hydroxy-3,5-dimethoxyphenyl)-2-propenoyl]phenyl-2,3-dihydro-1H-2-imidazolone;
(11g) 1-3-[(E)-3-(4-hydroxy-3,5-dimethoxyphenyl)-2-propenoyl]phenyl-4-(4-methylphenyl)-2,3-dihydro-1H-2-imidazolone;
(11h) 4-(3,4-dimethylphenyl)-1-3-[(E)-3-(4-hydroxy-3,5-dimethoxyphenyl)-2-propenoyl]phenyl-2,3-dihydro-1H-2-imidazolone;
(11i) 1-3-[(E)-3-(4-hydroxy-3,5-dimethoxyphenyl)-2-propenoyl]phenyl-4-(3,4,5-trimethylphenyl)-2,3-dihydro-1H-2-imidazolone;
(11j) 1-3-[(E)-3-(4-hydroxy-3,5-dimethoxyphenyl)-2-propenoyl]phenyl-4-(4-hydroxyphenyl)-2,3-dihydro-1H-2-imidazolone;
(12a) 1-3-[(E)-3-(4-hydroxy-3-methoxyphenyl)-2-propenoyl]phenyl-4-(2-naphthyl)-2,3-dihydro-1H-2-imidazolone;
(12b) 1-3-[(E)-3-(3-hydroxyphenyl)-2-propenoyl]phenyl-4-(2-naphthyl)-2,3-dihydro-1H-2-imidazolone;
(12c) 4-(2-naphthyl)-1-3-[(E)-3-(3,4,5-trimethoxyphenyl)-2-propenoyl]phenyl-2,3-dihydro-1H-2-imidazolone;
(12d) 1-3-[(E)-3-(3,4-dimethoxyphenyl)-2-propenoyl]phenyl-4-(2-naphthyl)-2,3-dihydro-1H-2-imidazolone;
(12e) 1-3-[(E)-3-(4-methoxyphenyl)-2-propenoyl]phenyl-4-(2-naphthyl)-2,3-dihydro-1H-2-imidazolone;
(12f) 4-(2-naphthyl)-1-3-[(E)-3-phenyl-2-propenoyl]phenyl-2,3-dihydro-1H-2-imidazolone;
(12g) 1-3-[(E)-3-(4-fluorophenyl)-2-propenoyl]phenyl-4-(2-naphthyl)-2,3-dihydro-1H-2-imidazolone;
(12h) 1-3-[(E)-3-(4-chlorophenyl)-2-propenoyl]phenyl-4-(2-naphthyl)-2,3-dihydro-1H-2-imidazolone;
(12i) 1-3-[(E)-3-(4-hydroxy-3,5-dimethoxyphenyl)-2-propenoyl]phenyl-4-(2-naphthyl)-2,3-dihydro-1H-2-imidazolone;
(13a) 1-3-[(E)-3-(4-hydroxy-3-methoxyphenyl)-2-propenoyl]phenyl-4-(3-pyridyl)-2,3-dihydro-1H-2-imidazolone;
(13b) 1-3-[(E)-3-(3-hydroxyphenyl)-2-propenoyl]phenyl-4-(3-pyridyl)-2,3-dihydro-1H-2-imidazolone;
(13c) 4-(3-pyridyl)-1-3-[(E)-3-(3,4,5-trimethoxyphenyl)-2-propenoyl]phenyl-2,3-dihydro-1H-2-imidazolone;
(13d) 1-3-[(E)-3-(3,4-dimethoxyphenyl)-2-propenoyl]phenyl-4-(3-pyridyl)-2,3-dihydro-1H-2-imidazolone;
(13e) 1-3-[(E)-3-(4-methoxyphenyl)-2-propenoyl]phenyl-4-(3-pyridyl)-2,3-dihydro-1H-2-imidazolone;
(13f) 1-3-[(E)-3-phenyl-2-propenoyl]phenyl-4-(3-pyridyl)-2,3-dihydro-1H-2-imidazolone;
(13g) 1-3-[(E)-3-(4-fluorophenyl)-2-propenoyl]phenyl-4-(3-pyridyl)-2,3-dihydro-1H-2-imidazolone;
(13h) 1-3-[(E)-3-(4-chlorophenyl)-2-propenoyl]phenyl-4-(3-pyridyl)-2,3-dihydro-1H-2-imidazolone;
(13i) 1-3-[(E)-3-(4-hydroxy-3,5-dimethoxyphenyl)-2-propenoyl]phenyl-4-(3-pyridyl)-2,3-dihydro-1H-2-imidazolone;
(14a) 4-(2-furyl)-1-3-[(E)-3-(4-hydroxy-3-methoxyphenyl)-2-propenoyl]phenyl-2,3-dihydro-1H-2-imidazolone;
(14b) 4-(2-furyl)-1-3-[(E)-3-(3-hydroxyphenyl)-2-propenoyl]phenyl-2,3-dihydro-1H-2-imidazolone;
(14c) 4-(2-furyl)-1-3-[(E)-3-(3,4,5-trimethoxyphenyl)-2-propenoyl]phenyl-2,3-dihydro-1H-2-imidazolone;
(14d) 1-3-[(E)-3-(3,4-dimethoxyphenyl)-2-propenoyl]phenyl-4-(2-furyl)-2,3-dihydro-1H-2-imidazolone;
(14e) 4-(2-furyl)-1-3-[(E)-3-(4-methoxyphenyl)-2-propenoyl]phenyl-2,3-dihydro-1H-2-imidazolone;
(14f) 4-(2-furyl)-1-3-[(E)-3-phenyl-2-propenoyl]phenyl-2,3-dihydro-1H-2-imidazolone;
(14g) 1-3-[(E)-3-(4-fluorophenyl)-2-propenoyl]phenyl-4-(2-furyl)-2,3-dihydro-1H-2-imidazolone;
(14h) 1-3-[(E)-3-(4-chlorophenyl)-2-propenoyl]phenyl-4-(2-furyl)-2,3-dihydro-1H-2-imidazolone;
(14i) 4-(2-furyl)-1-3-[(E)-3-(4-hydroxy-3,5-dimethoxyphenyl)-2-propenoyl]phenyl-2,3-dihydro-1H-2-imidazolone;
(15a) 4-(5-chloro-2-furyl)-1-3-[(E)-3-(4-hydroxy-3-methoxyphenyl)-2-propenoyl]phenyl-2,3-dihydro-1H-2-imidazolone;
(15b) 4-(5-chloro-2-furyl)-1-3-[(E)-3-(3-hydroxyphenyl)-2-propenoyl]phenyl-2,3-dihydro-1H-2-imidazolone;

(15c) 4-(5-chloro-2-furyl)-1-3-[(E)-3-(3,4,5-trimethoxyphenyl)-2-propenoyl]phenyl-2,3-dihydro-1H-2-imidazolone;
(15d) 4-(5-chloro-2-furyl)-1-3-[(E)-3-(3,4-diethoxyphenyl)-2-propenoyl]phenyl-2,3-dihydro-1H-2-imidazolone;
(15e) 4-(5-chloro-2-furyl)-1-3-[(E)-3-(4-methoxyphenyl)-2-propenoyl]phenyl-2,3-dihydro-1H-2-imidazolone;
(15f) 4-(5-chloro-2-furyl)-1-3-[(E)-3-phenyl-2-propenoyl]phenyl-2,3-dihydro-1H-2-imidazolone;
(15g) 4-(5-chloro-2-furyl)-1-3-[(E)-3-(4-fluorophenyl)-2-propenoyl]phenyl-2,3-dihydro-1H-2-imidazolone;
(15h) 4-(5-chloro-2-furyl)-1-3-[(E)-3-(4-chlorophenyl)-2-propenoyl]phenyl-2,3-dihydro-1H-2-imidazolone;
(15i) 4-(5-chloro-2-furyl)-1-3-[(E)-3-(4-hydroxy-3,5-dimethoxyphenyl)-2-propenoyl]phenyl-2,3-dihydro-1H-2-imidazolone;
(16a) 1-3-[(E)-3-(4-hydroxy-3-methoxyphenyl)-2-propenoyl]phenyl-4-(5-methyl-2-furyl)-2,3-dihydro-1H-2-imidazolone;
(16b) 1-3-[(E)-3-(3-hydroxyphenyl)-2-propenoyl]phenyl-4-(5-methyl-2-furyl)-2,3-dihydro-1H-2-imidazolone;
(16c) 4-(5-methyl-2-furyl)-1-3-[(E)-3-(3,4,5-trimethoxyphenyl)-2-propenoyl]phenyl-2,3-dihydro-1H-2-imidazolone;
(16d) 1-3-[(E)-3-(3,4-dimethoxyphenyl)-2-propenoyl]phenyl-4-(5-methyl-2-furyl)-2,3-dihydro-1H-2-imidazolone;
(16e) 1-3-[(E)-3-(4-methoxyphenyl)-2-propenoyl]phenyl-4-(5-methyl-2-furyl)-2,3-dihydro-1H-2-imidazolone;
(16f) 4-(5-methyl-2-furyl)-1-3-[(E)-3-phenyl-2-propenoyl]phenyl-2,3-dihydro-1H-2-imidazolone;
(16g) 1-3-[(E)-3-(4-fluorophenyl)-2-propenoyl]phenyl-4-(5-methyl-2-furyl)-2,3-dihydro-1H-2-imidazolone;
(16h) 1-3-[(E)-3-(4-chlorophenyl)-2-propenoyl]phenyl-4-(5-methyl-2-furyl)-2,3-dihydro-1H-2-imidazolone;
(16i) 1-3-[(E)-3-(4-hydroxy-3,5-dimethoxyphenyl)-2-propenoyl]phenyl-4-(5-methyl-2-furyl)-2,3-dihydro-1H-2-imidazolone;
(17a) 1-3-[(E)-3-(4-hydroxy-3-methoxyphenyl)-2-propenoyl]phenyl-4-(2-thienyl)-2,3-dihydro-1H-2-imidazolone;
(17b) 1-3-[(E)-3-(3-hydroxyphenyl)-2-propenoyl]phenyl-4-(2-thienyl)-2,3-dihydro-1H-2-imidazolone;
(17c) 4-(2-thienyl)-1-3-[(E)-3-(3,4,5-trimethoxyphenyl)-2-propenoyl]phenyl-2,3-dihydro-1H-2-imidazolone;
(17d) 1-3-[(E)-3-(3,4-dimethoxyphenyl)-2-propenoyl]phenyl-4-(2-thienyl)-2,3-dihydro-1H-2-imidazolone;
(17e) 1-3-[(E)-3-(4-methoxyphenyl)-2-propenoyl]phenyl-4-(2-thienyl)-2,3-dihydro-1H-2-imidazolone;
(17f) 1-3-[(E)-3-phenyl-2-propenoyl]phenyl-4-(2-thienyl)-2,3-dihydro-1H-2-imidazolone;
(17g) 1-3-[(E)-3-(4-fluorophenyl)-2-propenoyl]phenyl-4-(2-thienyl)-2,3-dihydro-1H-2-imidazolone;
(17h) 1-3-[(E)-3-(4-chlorophenyl)-2-propenoyl]phenyl-4-(2-thienyl)-2,3-dihydro-1H-2-imidazolone;
(17i) 1-3-[(E)-3-(4-hydroxy-3,5-dimethoxyphenyl)-2-propenoyl]phenyl-4-(2-thienyl)-2,3-dihydro-1H-2-imidazolone;
(18a) 4-(5-chloro-2-thienyl)-1-3-[(E)-3-(4-hydroxy-3-methoxyphenyl)-2-propenoyl]phenyl-2,3-dihydro-1H-2-imidazolone;
(18b) 4-(5-chloro-2-thienyl)-1-3-[(E)-3-(3-hydroxyphenyl)-2-propenoyl]phenyl-2,3-dihydro-1H-2-imidazolone;
(18c) 4-(5-chloro-2-thienyl)-1-3-[(E)-3-(3,4,5-trimethoxyphenyl)-2-propenoyl]phenyl-2,3-dihydro-1H-2-imidazolone;
(18d) 4-(5-chloro-2-thienyl)-1-3-[(E)-3-(3,4-dimethoxyphenyl)-2-propenoyl]phenyl-2,3-dihydro-1H-2-imidazolone;
(18e) 4-(5-chloro-2-thienyl)-1-3-[(E)-3-(4-methoxyphenyl)-2-propenoyl]phenyl-2,3-dihydro-1H-2-imidazolone;
(18f) 4-(5-chloro-2-thienyl)-1-3-[(E)-3-phenyl-2-propenoyl]phenyl-2,3-dihydro-1H-2-imidazolone;
(18g) 4-(5-chloro-2-thienyl)-1-3-[(E)-3-(4-fluorophenyl)-2-propenoyl]phenyl-2,3-dihydro-1H-2-imidazolone;
(18h) 1-3-[(E)-3-(4-chlorophenyl)-2-propenoyl]phenyl-4-(5-chloro-2-thienyl)-2,3-dihydro-1H-2-imidazolone;
(18i) 4-(5-chloro-2-thienyl)-1-3-[(E)-3-(4-hydroxy-3,5-dimethoxyphenyl)-2-propenoyl]phenyl-2,3-dihydro-1H-2-imidazolone;
(19a) 1-3-[(E)-3-(4-hydroxy-3-methoxyphenyl)-2-propenoyl]phenyl-4-(5-methyl-2-thienyl)-2,3-dihydro-1H-2-imidazolone;
(19b) 1-3-[(E)-3-(3-hydroxyphenyl)-2-propenoyl]phenyl-4-(5-methyl-2-thienyl)-2,3-dihydro-1H-2-imidazolone;
(19c) 4-(5-methyl-2-thienyl)-1-3-[(E)-3-(3,4,5-trimethoxyphenyl)-2-propenoyl]phenyl-2,3-dihydro-1H-2-imidazolone;
(19d) 1-3-[(E)-3-(3,4-dimethoxyphenyl)-2-propenoyl]phenyl-4-(5-methyl-2-thienyl)-2,3-dihydro-1H-2-imidazolone;
(19e) 1-3-[(E)-3-(4-methoxyphenyl)-2-propenoyl]phenyl-4-(5-methyl-2-thienyl)-2,3-dihydro-1H-2-imidazolone;
(19f) 4-(5-methyl-2-thienyl)-1-3-[(E)-3-phenyl-2-propenoyl]phenyl-2,3-dihydro-1H-2-imidazolone;
(19g) 1-3-[(E)-3-(4-fluorophenyl)-2-propenoyl]phenyl-4-(5-methyl-2-thienyl)-2,3-dihydro-1H-2-imidazolone;
(19h) 1-3-[(E)-3-(4-chlorophenyl)-2-propenoyl]phenyl-4-(5-methyl-2-thienyl)-2,3-dihydro-1H-2-imidazolone;
(19i) 1-3-[(E)-3-(4-hydroxy-3,5-dimethoxyphenyl)-2-propenoyl]phenyl-4-(5-methyl-2-thienyl)-2,3-dihydro-1H-2-imidazolone.

3. The chalcone linked imidazolone compound as claimed in claim 1, wherein the compound is represented by one of the following structural formulae:

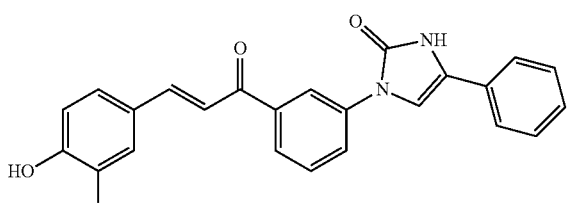

3a

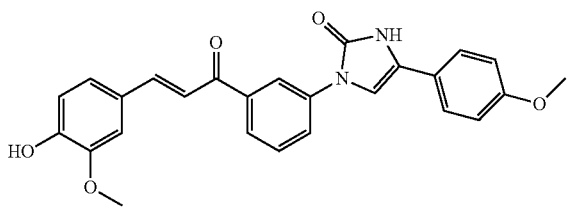

3b

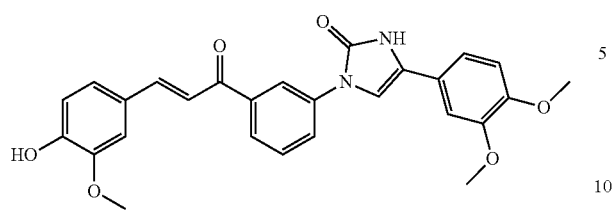
3c
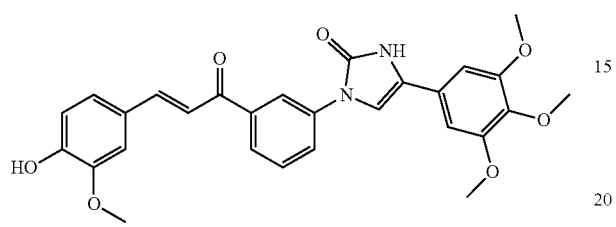
3d
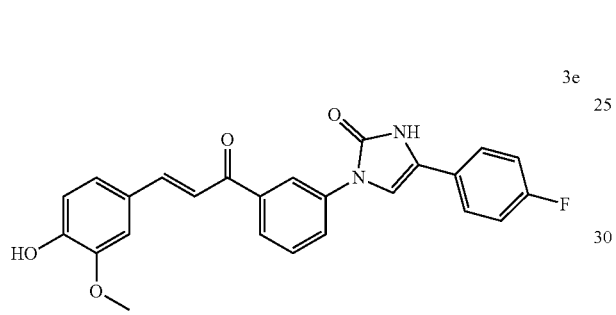
3e
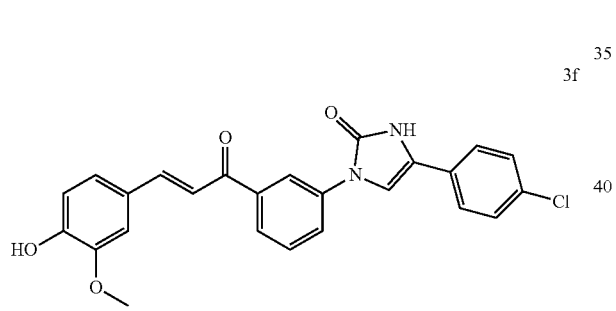
3f
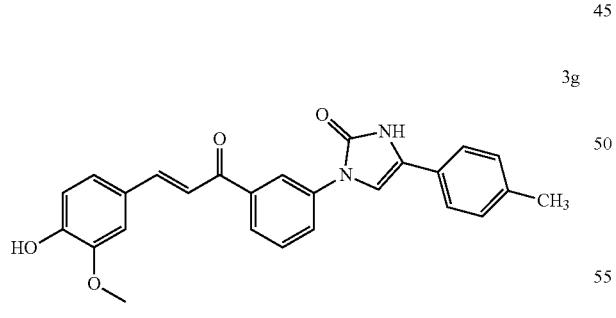
3g
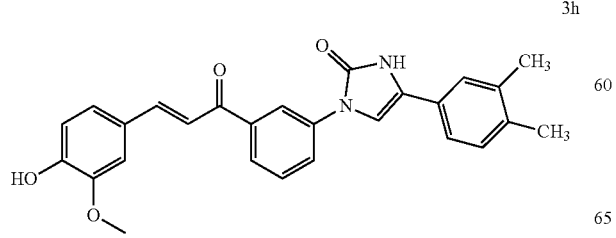
3h
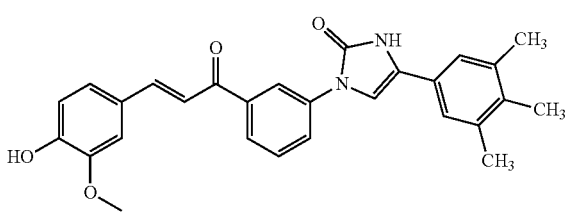
3i
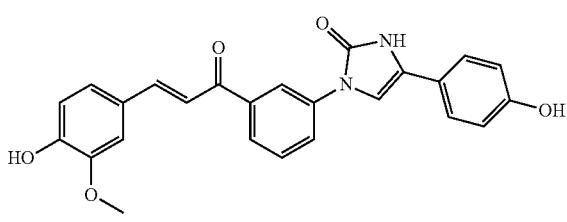
3j
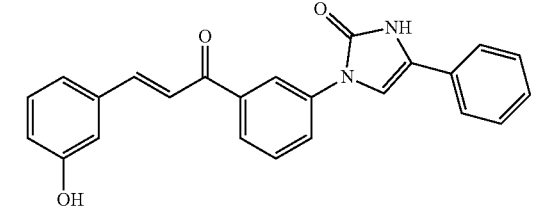
4a
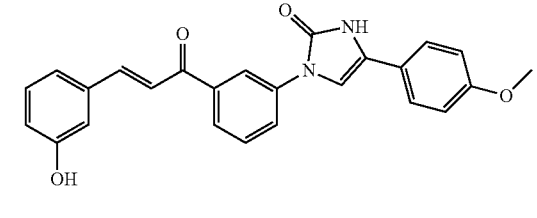
4b
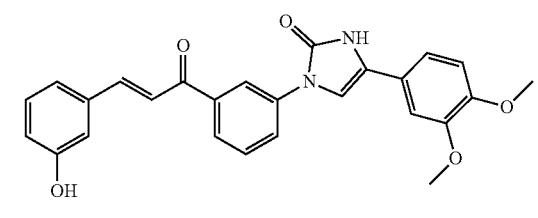
4c
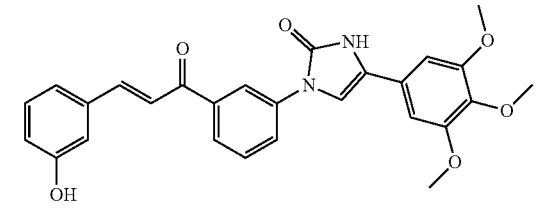
4d
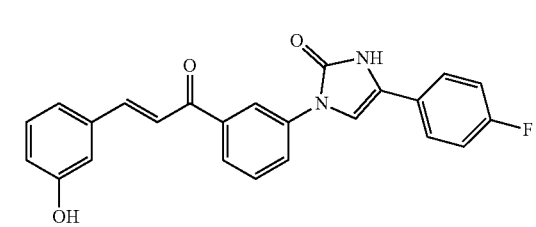
4e -continued
4f
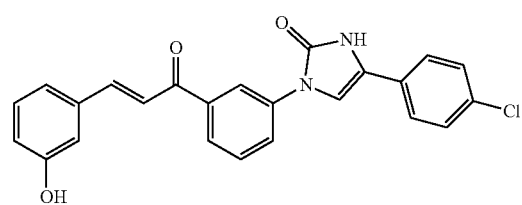
4g
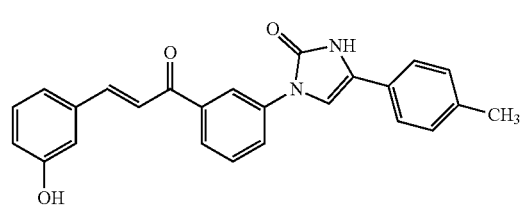
4h
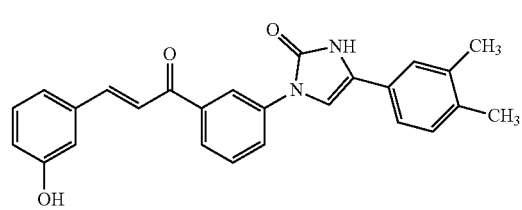
4i
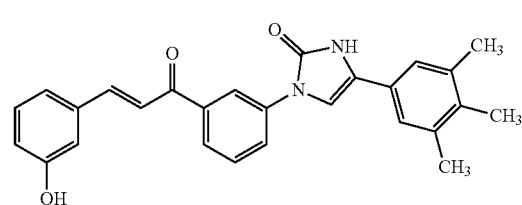
4j
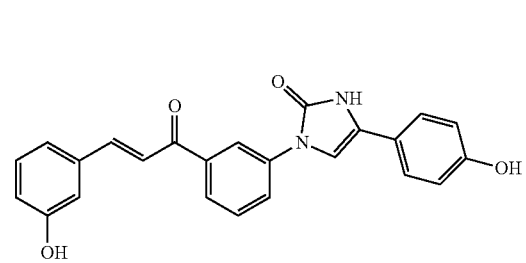
5a
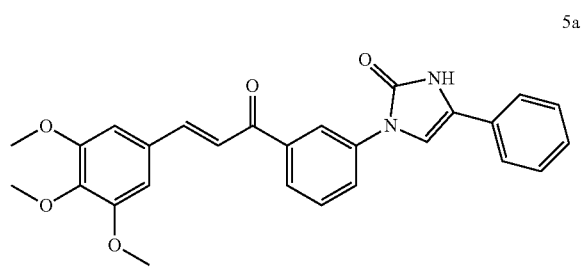
5b
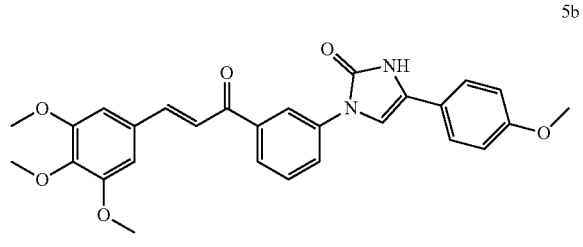
-continued
5c
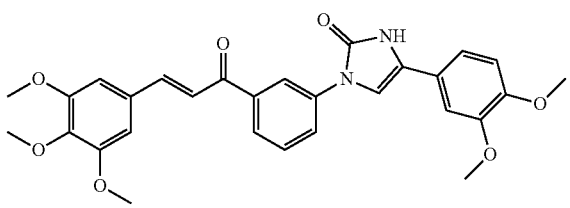
5d
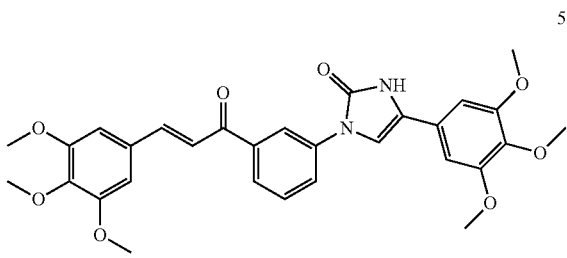
5e
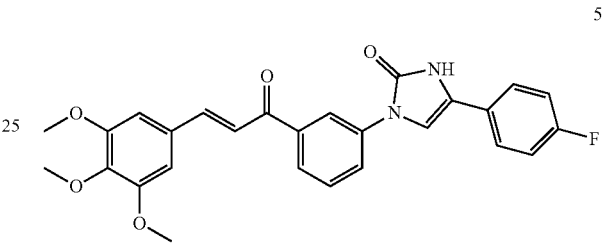
5f
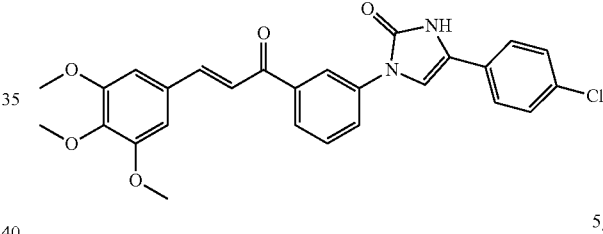
5g
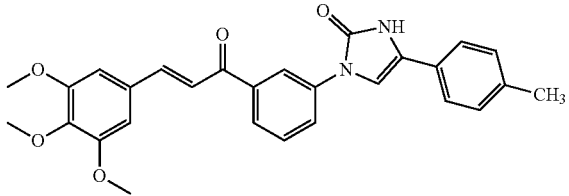
5h
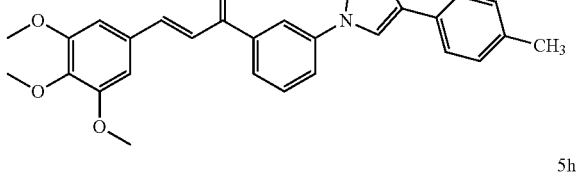
5i
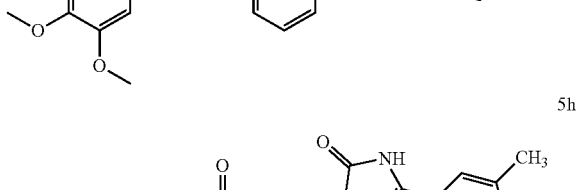

5j
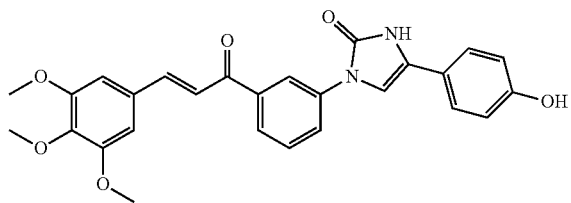
6a
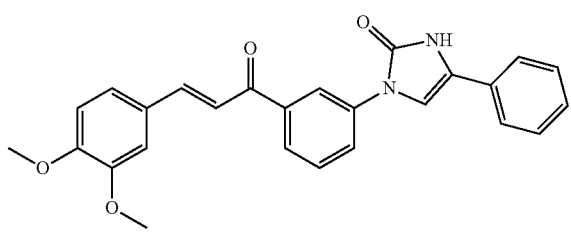
6b
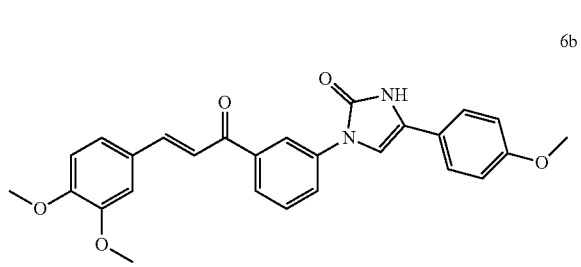
6c
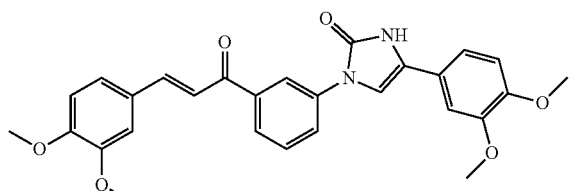
6d
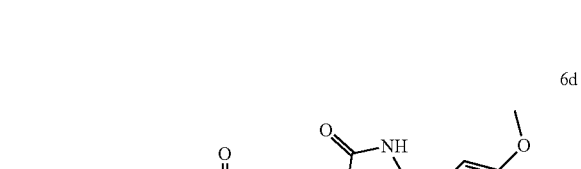
6e
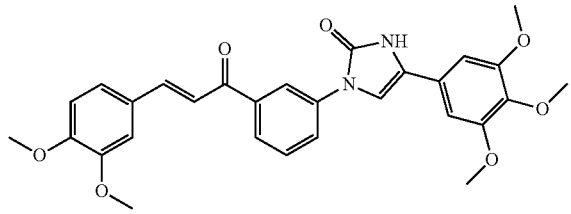
6f
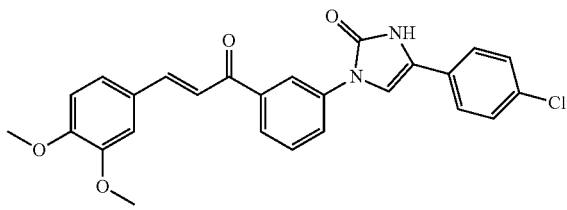
6g
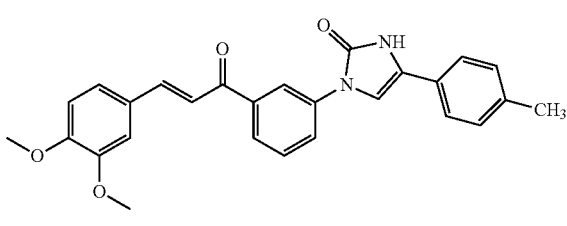
6h
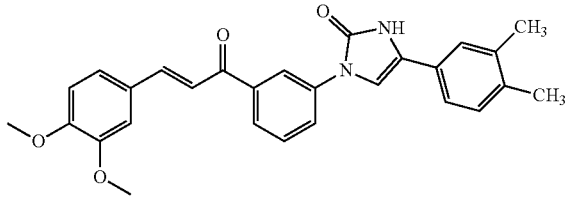
6i
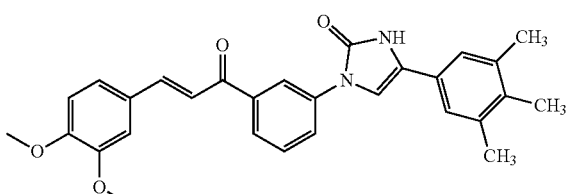
6j
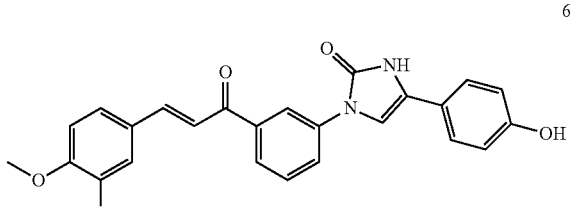
7a
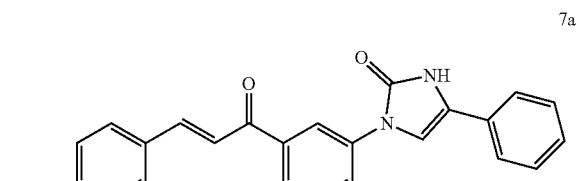
7b
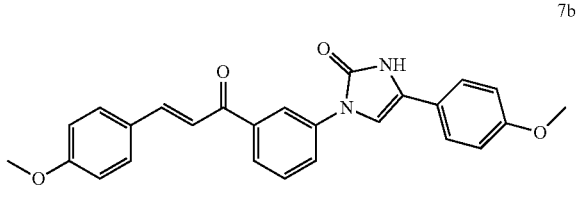

7c
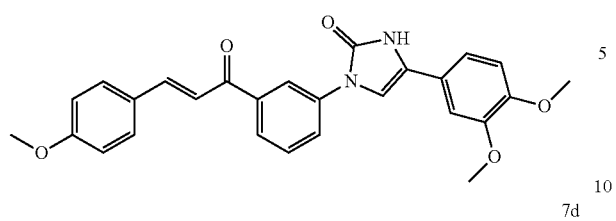
7d
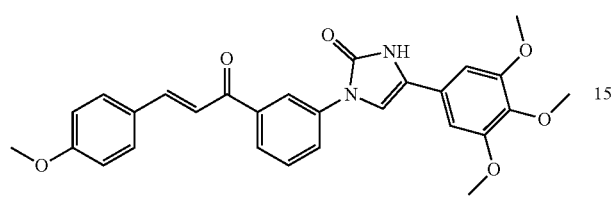
7e
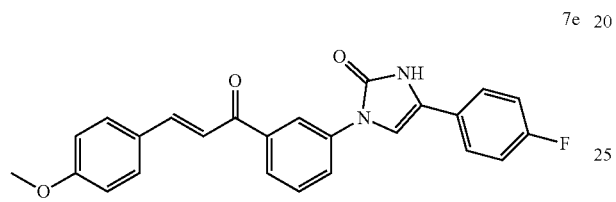
7f
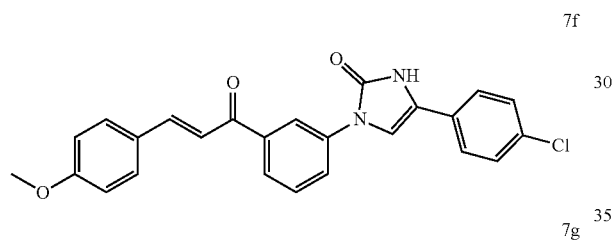
7g
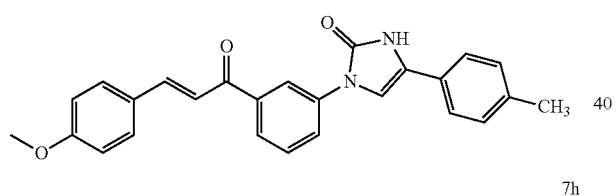
7h
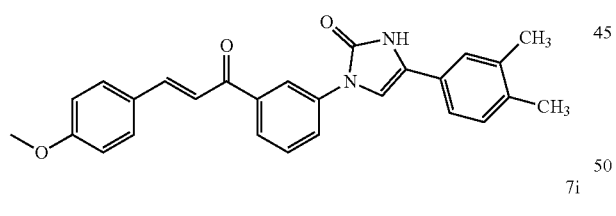
7i
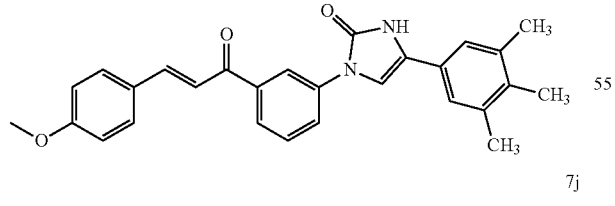
7j
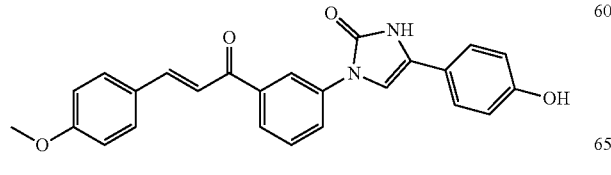
8a
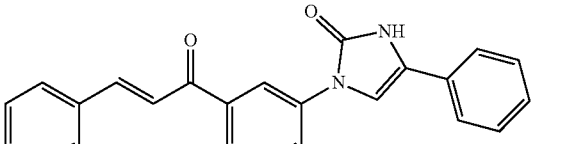
8b
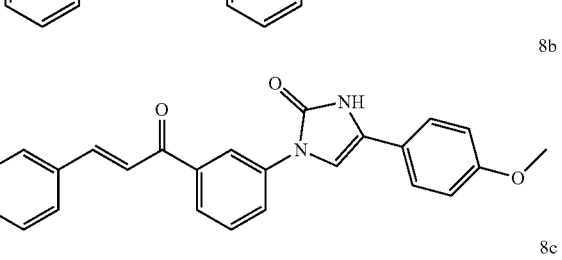
8c
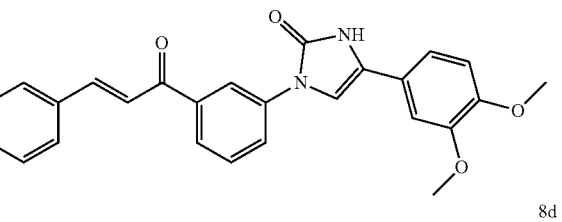
8d
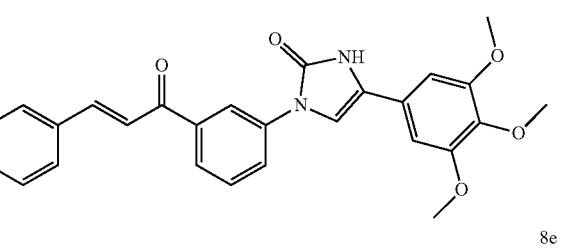
8e
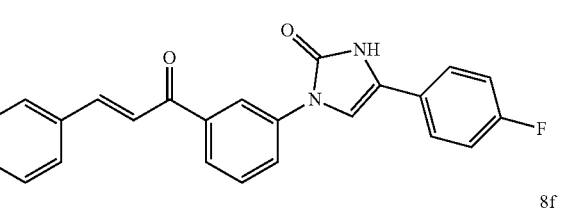
8f
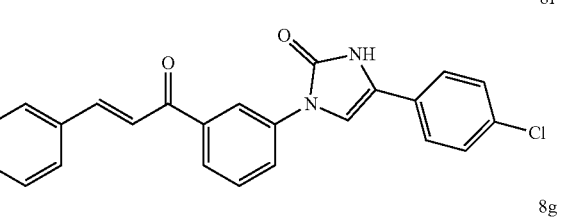
8g
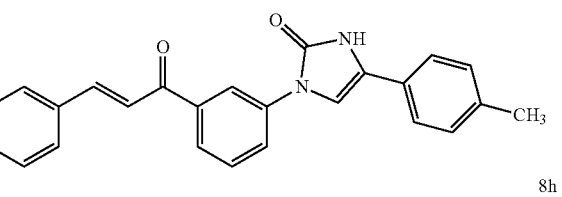
8h
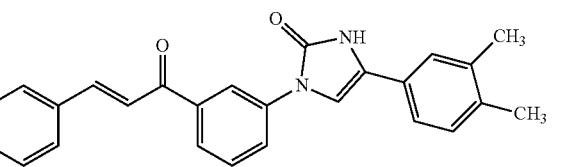

8i
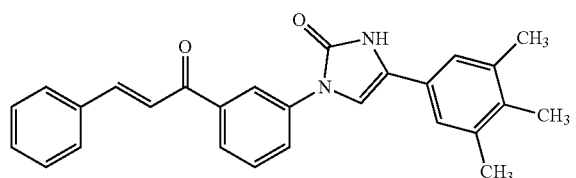
8j
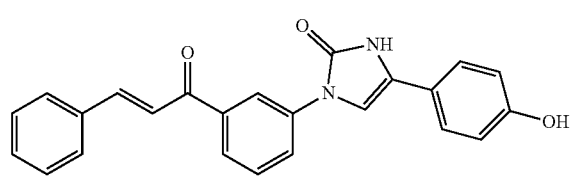
9a
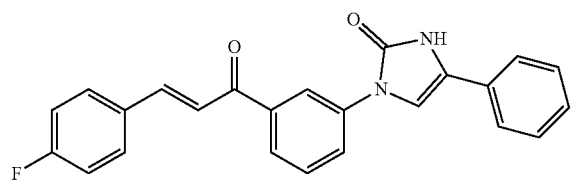
9b
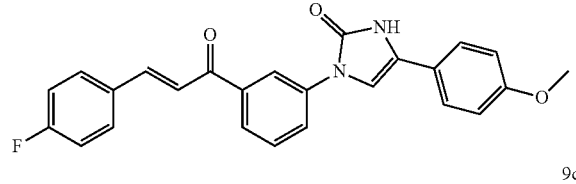
9c
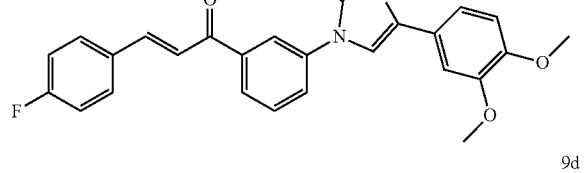
9d
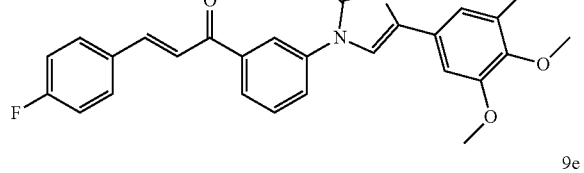
9e
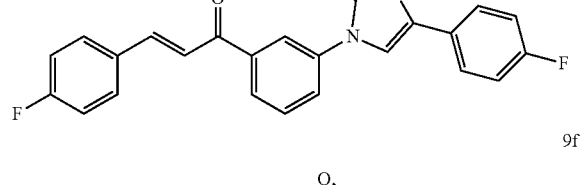
9f
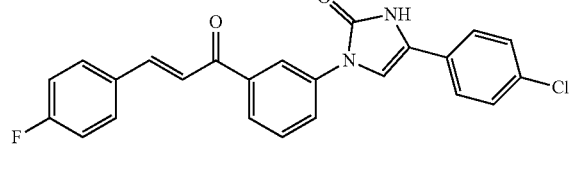
9g
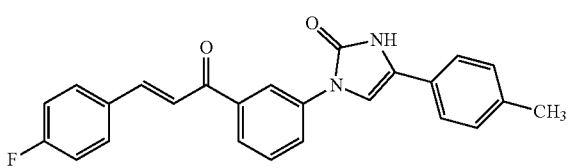
9h
9i
9j
10a
10b
10c
10d

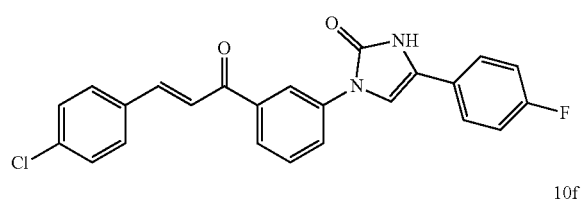
10e
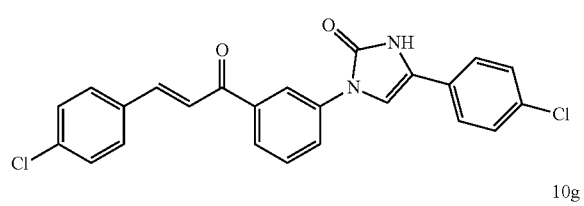
10f
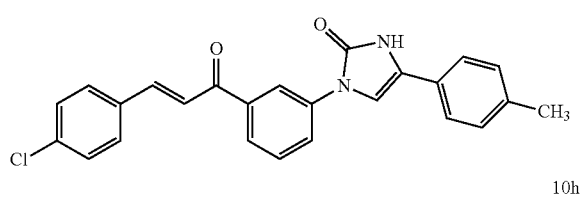
10g
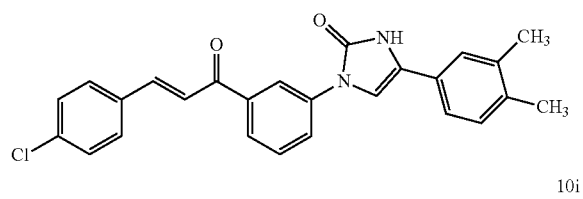
10h
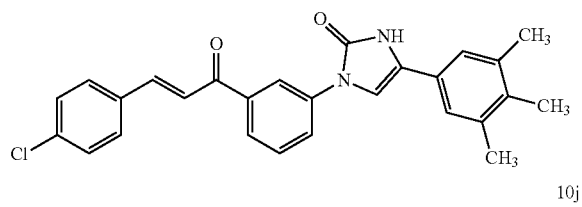
10i
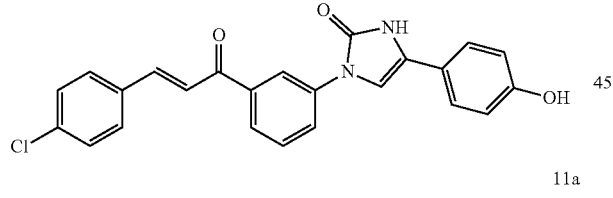
10j
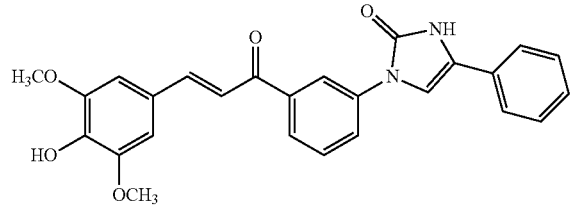
11a
11b
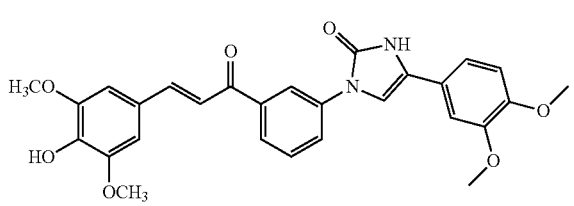
11c
11d
11e
11f
11g
11h
11i 11j 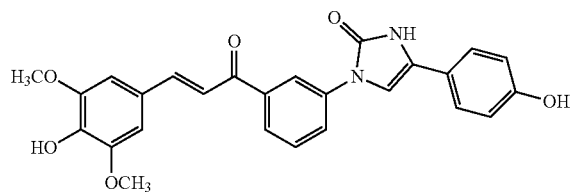
12a 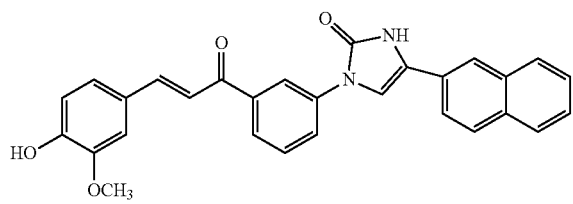
12b 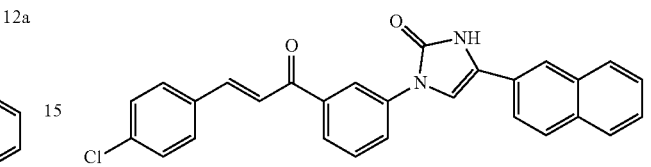
12c 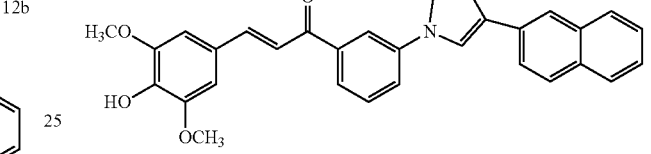
12d 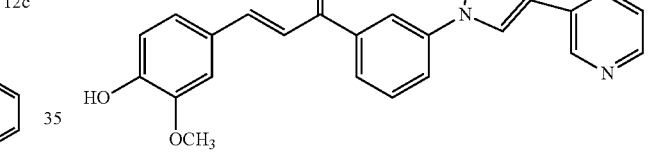
12e 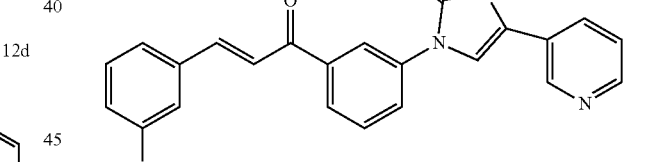
12f 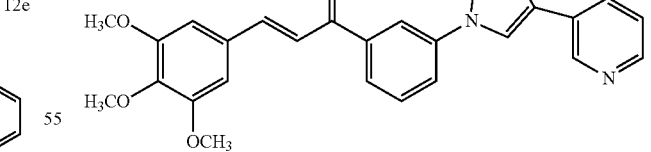
12g 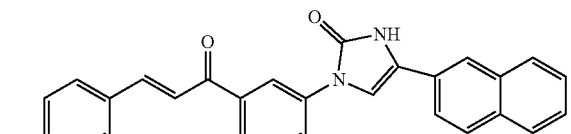
12h 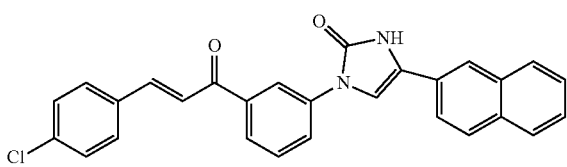
12i 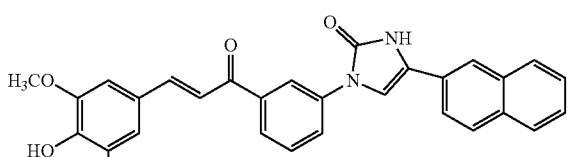
13a 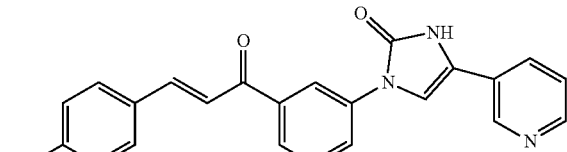
13b 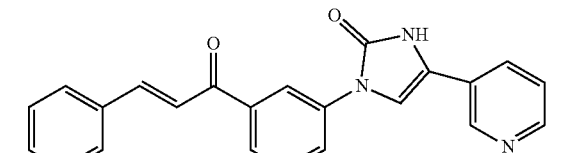
13c 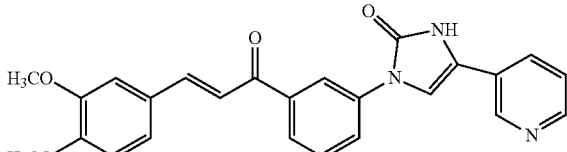
13d 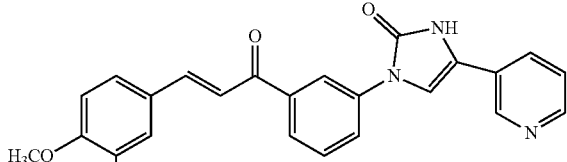

13e
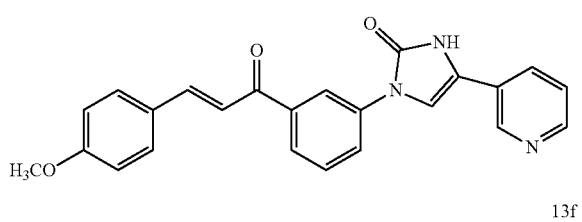
13f
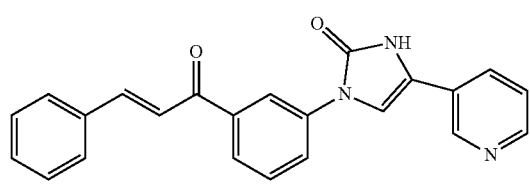
13g
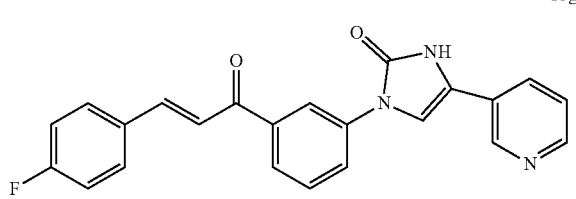
13h
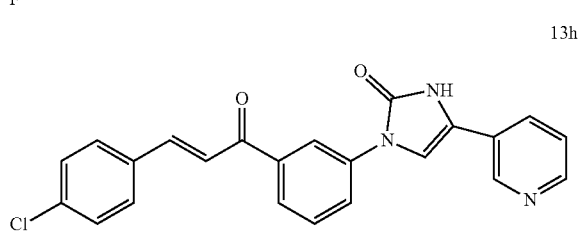
13i
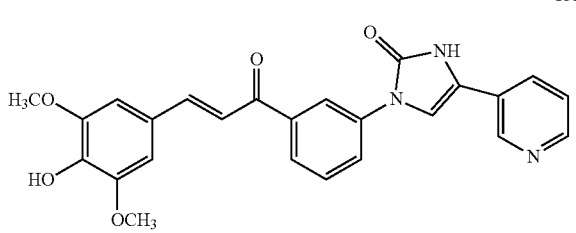
14a
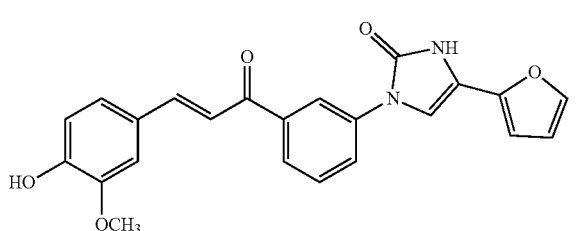
14b
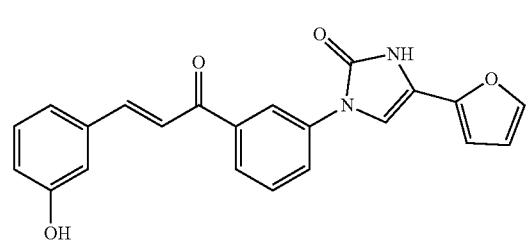
14c
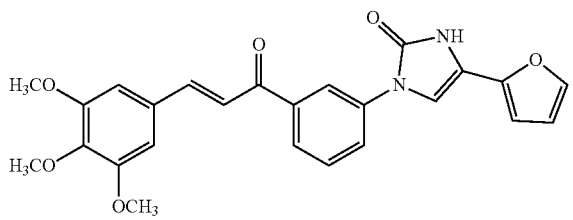
14d
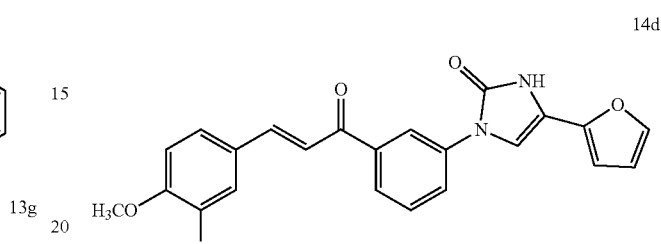
14e
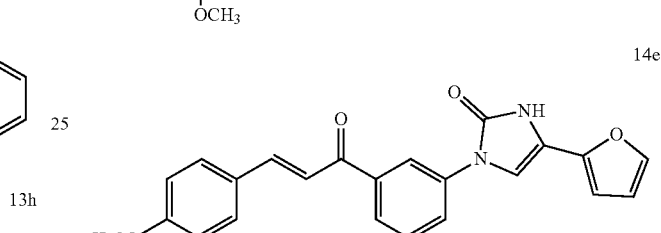
14f
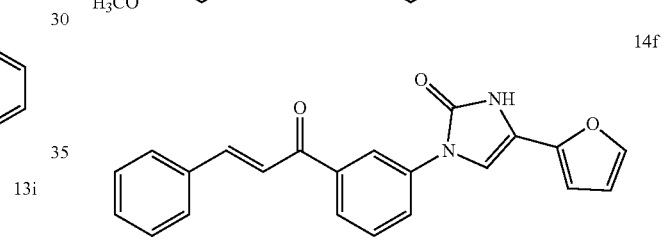
14g
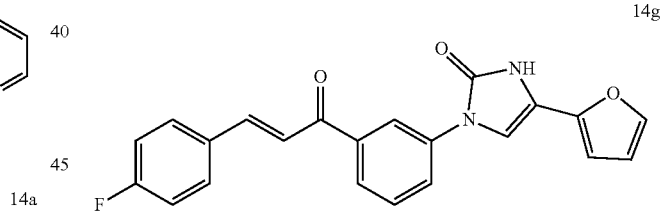
14h
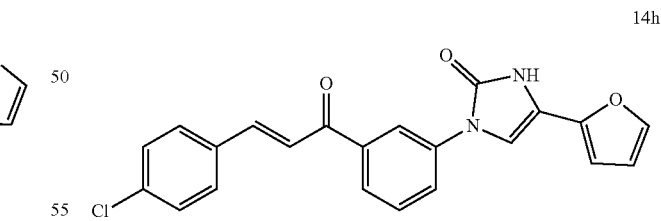
14i
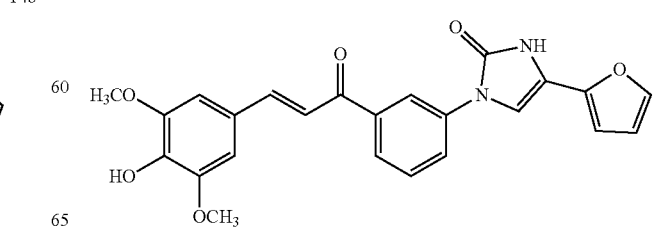

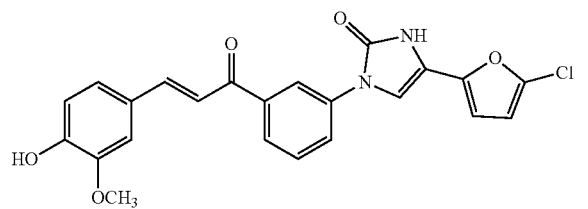
15a
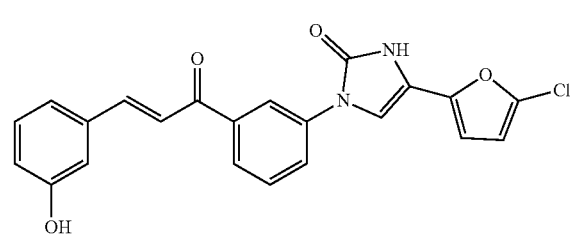
15b
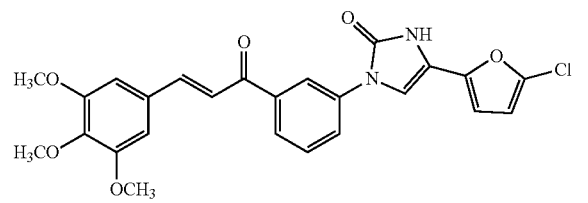
15c
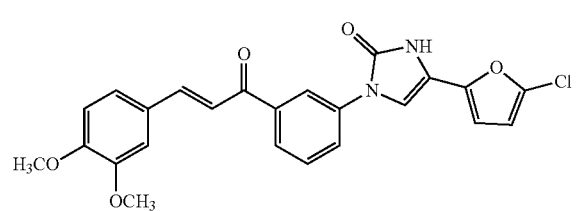
15d
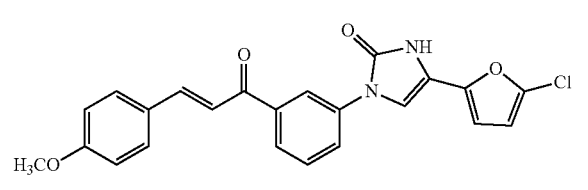
15e
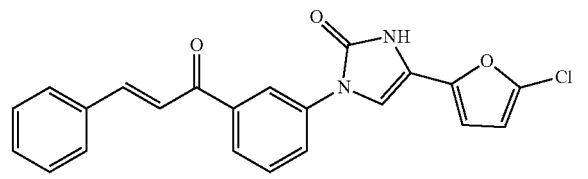
15f
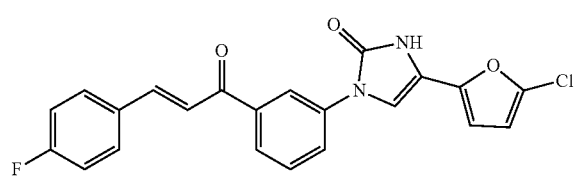
15g
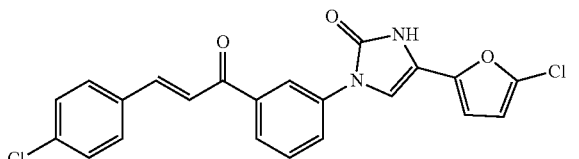
15h
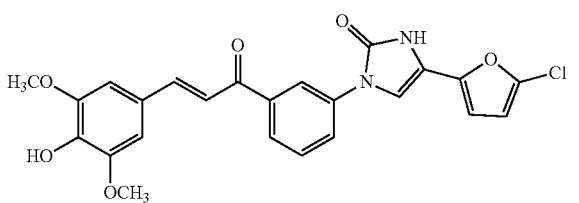
15i
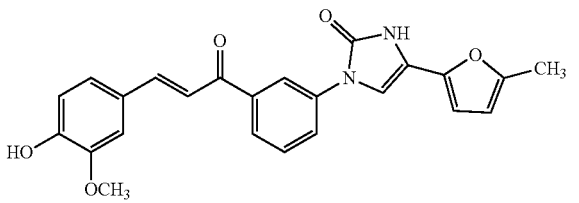
16a
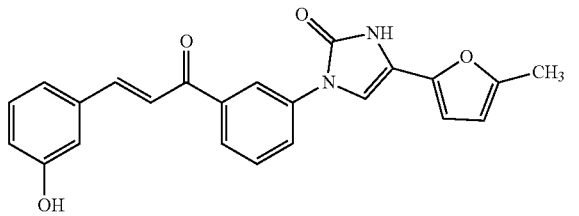
16b
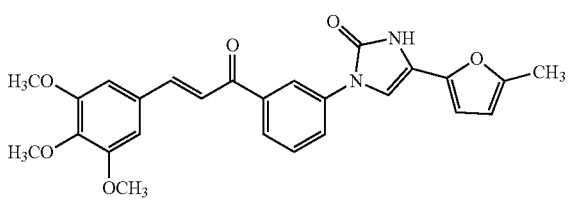
16c
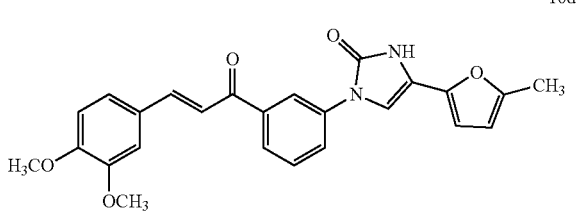
16d
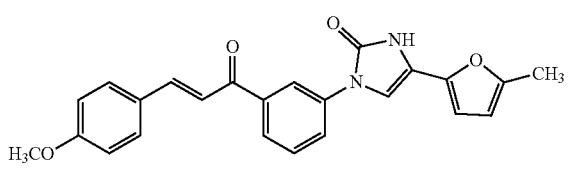
16e 16f 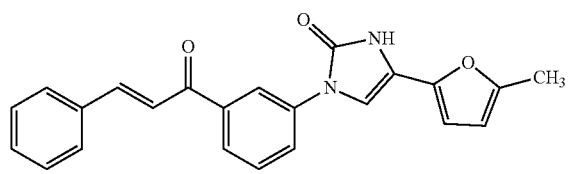
16g 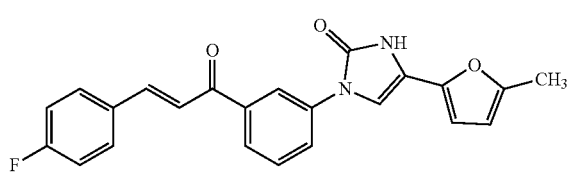
16h 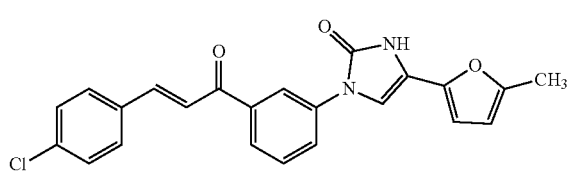
16i 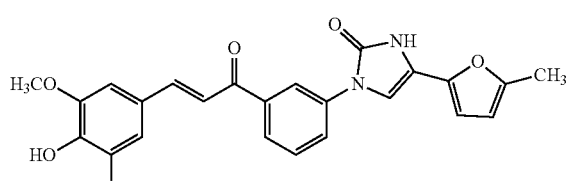
17a 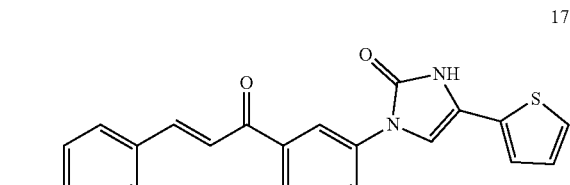
17b 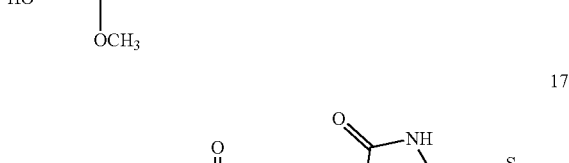
17c 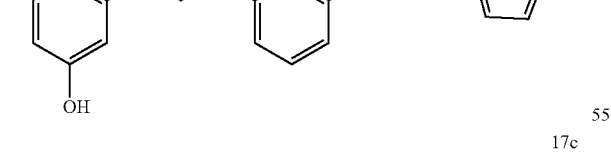
17d 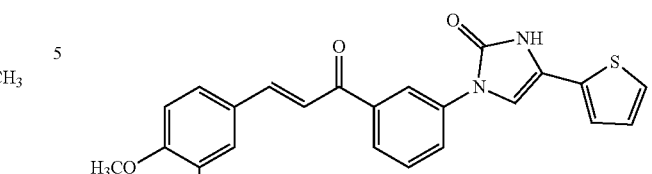
17e 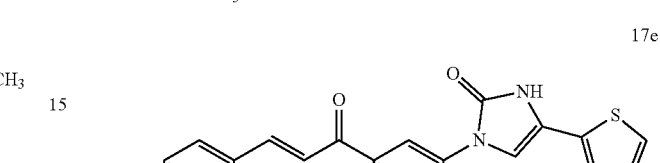
17f 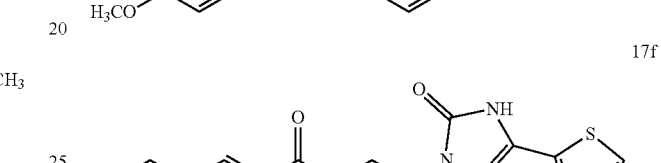
17g 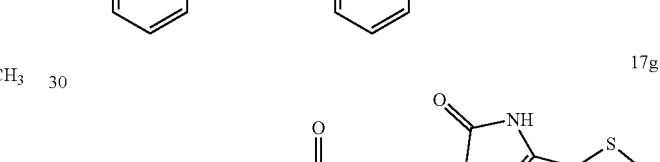
17h 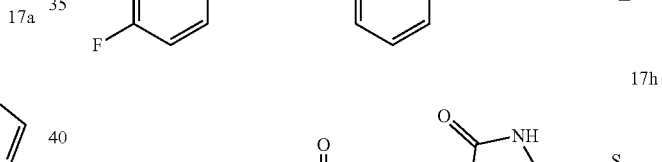
17i 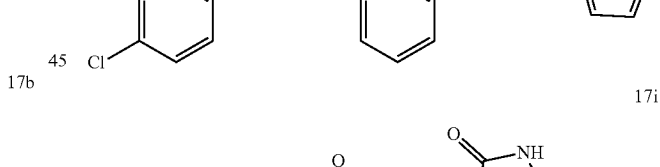
18a 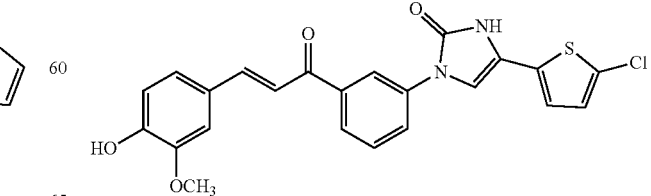

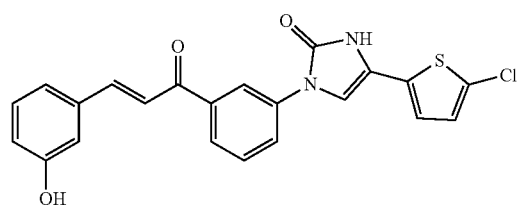
18b
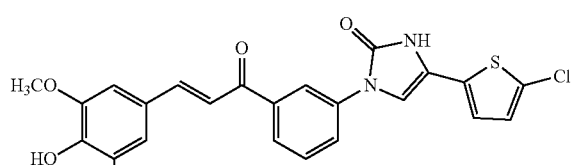
18i
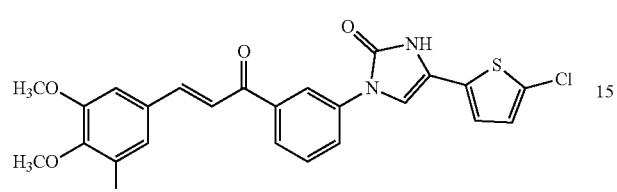
18c
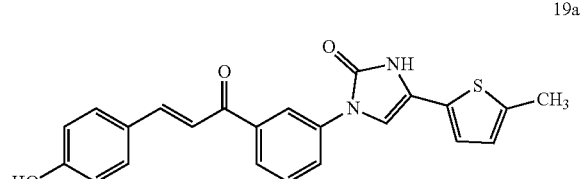
19a
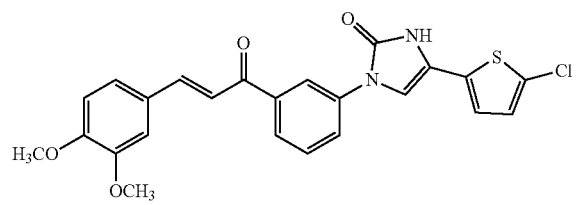
18d
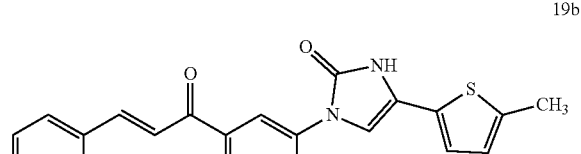
19b
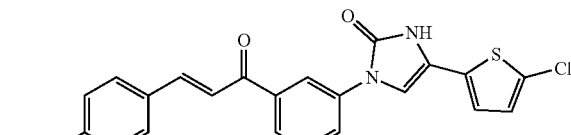
18e
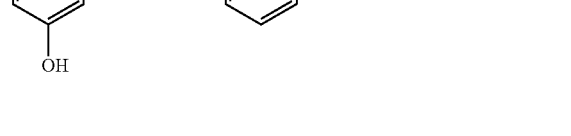
19c
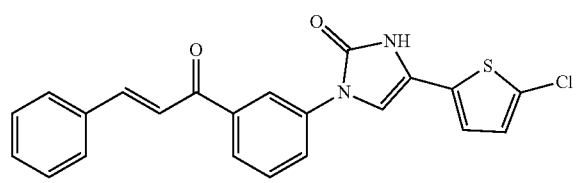
18f
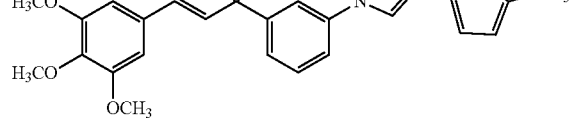
19d
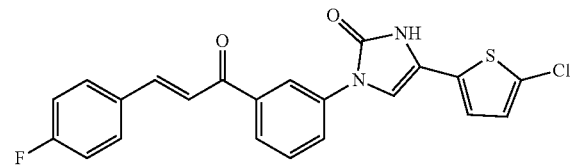
18g
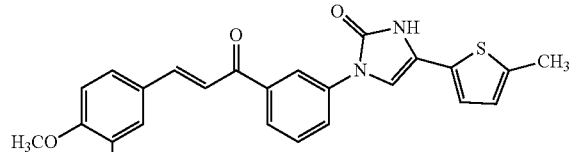
19e
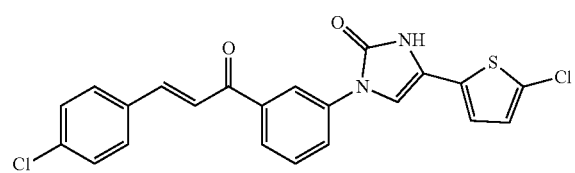
18h
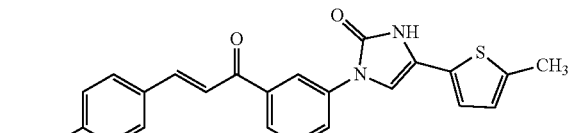
19f

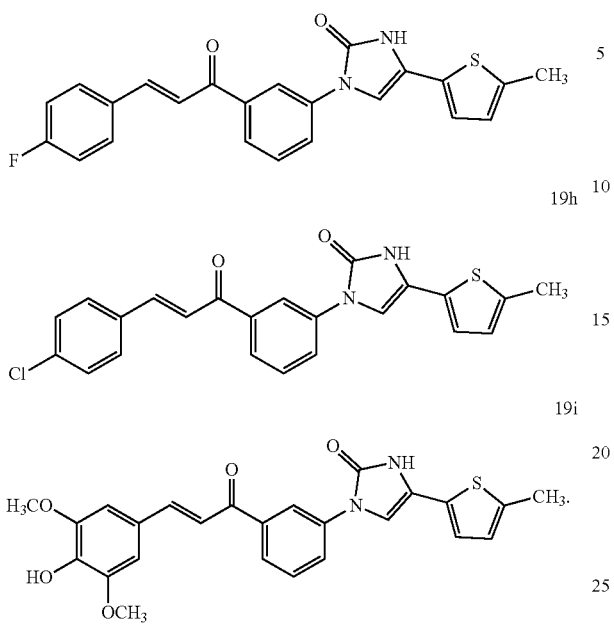

19g

19h

19i

4. A process for the preparation of chalcone linked imidazolone compound of formula A comprising the steps of:
  i stirring the solution of Ba(OH)$_2$.8H$_2$O in methanol;
  ii adding 3-aminoacetophenone and aldehyde 1a-i, wherein R represents hydrogen or methoxy, R1 represents hydrogen, methoxy, hydroxyl, chloro or fluoro and R2 represents hydrogen, methoxy or hydroxyl, to the stirred solution obtained in step i to obtain intermediate chalconoamine 20a-i, wherein R represents hydrogen or methoxy, R1 represents hydrogen, methoxy, hydroxyl, chloro or fluoro and R2 represents hydrogen, methoxy or hydroxyl;

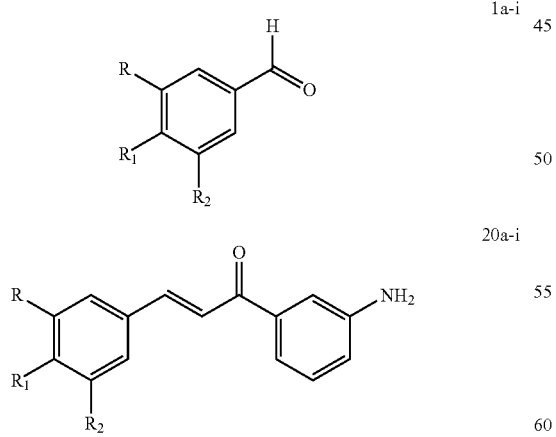

1a-i 20a-i iii reacting (E)-3-(3-aminophenyl)-1-phenyl-2-propen-1-one of formula 20a-i with substituted phenacyl bromide of formula 21a-j, 22, 23, or 23 to 29 in the presence of sodium bicarbonate in ethanol to obtain N-arylphenacylamines 30a-j to 38a-j or 39a-i to 46a-i;

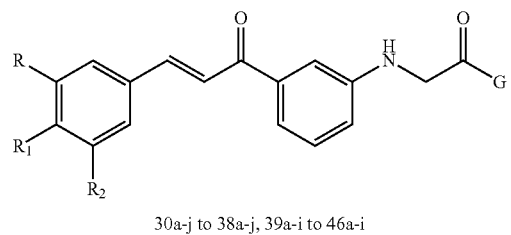

30a-j to 38a-j, 39a-i to 46a-i iv stirring the mixture of N-arylphenacylamine 30a-j to 38a-j or 39a-i to 46a-i and potassium cyanate in acetic acid; and
  v purifying by column chromatography using MeOH—CHCl$_3$ to give final compound of formula A Formula A

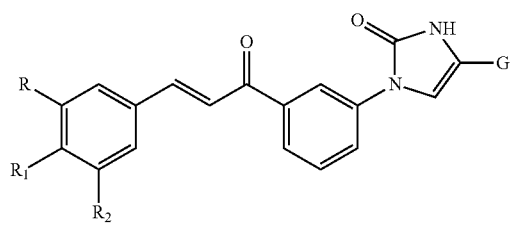

Wherein

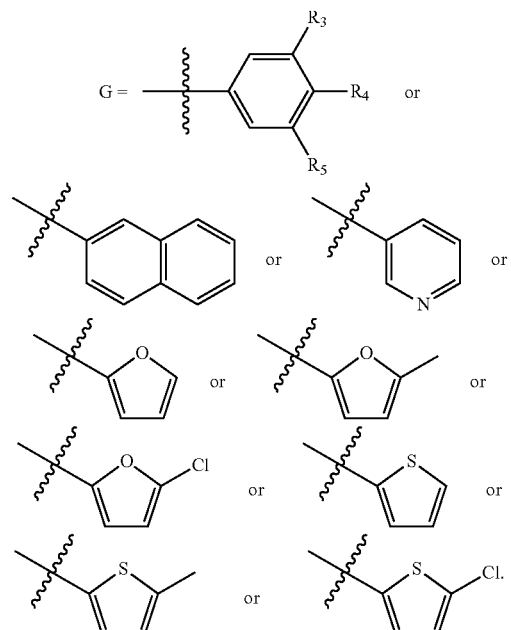

R = H, OMe
R$_1$ = H, Cl, F, OH, OMe
R$_2$ = H, OH, OMe
R$_3$ = H, OMe, CH$_3$
R$_4$ = H, Cl, F, OH, OMe, CH$_3$
R$_5$ = H, OMe, CH$_3$

5. The chalcone linked imidazolone compound of formula 3a, 3b, 3f, 4f, 5a, 5b, 5d, 5f or 12b as claimed in claim 3, exhibiting an in vitro anticancer activity against the standard fifty three human cancer cell lines derived from nine types of cancer which include leukemia cell line, non small cell lung cell line, colon cell line, CNS cell line, renal cell line, prostate cell line, ovarian cell line, breast and melanoma cell line.

6. The chalcone linked imidazolone compound of formula 3a, 3b, 3f, 4a, 4f, 5a, 5b, 5d, 5f or 12b as claimed in claim 3, exhibiting an in vitro anticancer activity against two leukemia cancer cell lines, RPMI-8226 and K-562, with $GI_{50}$ in the range of 1.67 to 2.04, 1.35 to 2.35, 1.33 to 1.42, 2.1+5 to 3.35, 0.40 to 1.55, 0.50 to 0.62, 0.92 to 1.27, 0.23 to 0.59, 3.69 to 3.92, and 1.43 to 1.67 μm, respectively, at an exposure period of at least 48 hrs.

7. The chalcone linked imidazolone compound of formula 3a, 3b, 3f, 4a, 4f, 5a, 5b, 5d, 5f or 12b as claimed in claim 3, exhibiting an in vitro anticancer activity against nine Non-small cell lung cancer cell lines, A549/ATCC, EKVX, HOP-62, HOP-92, NCI-H226, NCI-H23, NCI-H322M, NCI-H460, and NCI-H522, with $GI_{50}$ in the range of 1.48 to 3.90, 2.85 to 13.4, 1.26 to 9.61, 2.49 to 24.8, 1.60 to 3.55, 0.95 to 14.6, 1.56 to 35.2, 1.05 to 14.4, 3.56 to 85.2, and 0.51 to 3.38 μm, respectively, at an exposure period of at least 48 hrs.

8. The chalcone linked imidazolone compound of formula 3a, 3b, 3f, 4a, 4f, 5a, 5b, 5d, 5f or 12b as claimed in claim 3, exhibiting an in vitro anticancer activity against seven colon cancer cell lines, COLO 205, HCC-2998, HCT-116, HCT-15, HT29, KM12, and SW-620, with $GI_{50}$ in the range of 1.40 to 3.77, 1.77 to 6.61, 1.46 to 3.40, 1.83 to 4.09, 1.23 to 13.7, 0.33 to 1.51, 0.37 to 1.84, 0.74 to 1.92, 1.39 to 7.38, and 0.22 to 2.13 μm, respectively, at an exposure period of at least 48 hrs.

9. The chalcone linked imidazolone compound of formula 3a, 3b, 3f, 4a, 4f, 5a, 5b, 5d, 5f or 12b as claimed in claim 3, exhibiting an in vitro anticancer activity against six CNS cancer cell lines, SF-268, SF-295, SF-539, SNB-19, SNB-75, and U251, with $GI_{50}$ in the range of 1.91 to 3.90, 2.25 to 13.9, 1.78 to 10.5, 1.61 to 18.2, 0.58 to 1.92, 0.63 to 4.47, 0.88 to 4.95, 1.23 to 4.96, 2.12 to 24.3, and 1.09 to 1.88 μm, respectively, at an exposure period of at least 48 hrs.

10. The chalcone linked imidazolone compound of formula 3a, 3b, 3f, 4f, 5a, 5b, 5d, 5f or 12b as claimed in claim 3, exhibiting an in vitro anticancer activity against eight renal cancer cell lines, A498, 786-0, ACHN, CAKI-1, RXF 393, SN12C, TK-10, and UO-31, with $GI_{50}$ in the range of 1.35 to 5.29, 3.40 to 6.08, 1.67 to 6.40 1.89 to 14.3, 0.55 to 3.71, 1.38 to 3.02, 1.61 to 3.50, 0.96 to 20.3, 2.14 to 30.2, and 1.26 to 3.45 μm, respectively, at an exposure period of at least 48 hrs.

11. The chalcone linked imidazolone compound of formula 3a, 3b, 3f, 4a, 5a, 5b, 5d or 12b as claimed in claim 3, exhibiting an in vitro anticancer activity against prostate cancer cell line, PC-3, with $GI_{50}$ of 2.52, 3.05, 1.95, 2.82, 3.26, 6.22, 2.63, 16.5, and 1.85 μm, respectively, at an exposure period of at least 48 hrs.

12. The chalcone linked imidazolone compound of formula 3a, 3b, 3f, 4a, 4f, 5a, 5b, 5d, 5f or 12b as claimed in claim 3, exhibiting an in vitro anticancer activity against six ovarian cancer cell lines, OVCAR-3, OVCAR-4, OVCAR-5, OVCAR-8, NCI/ADR-RES, and SK-OV-3, with $GI_{50}$ in the range of 2.04 to 5.19, 2.56 to 6.08, 1.56 to 4.64, 2.80 to 11.1, 0.99 to 4.21, 1.10 to 3.27, 1.70 to 4.60, 1.48 to 5.12, 2.36 to 31.4, and 1.33 to 2.33 μm, respectively, at an exposure period of at least 48 hrs.

13. The chalcone linked imidazolone compound of formula 3a, 3b, 3f, 4a, 4f, 5a, 5b, 5d, 5f or 12b as claimed in claim 3, exhibiting an in vitro anticancer activity against five breast cancer cell lines, MCF7, MDA-MB-231/ATCC, HS 578T, BT-549, and TD-47D, with $GI_{50}$ in the range of 1.55 to 4.16, 3.18 to 5.25, 2.30 to 4.67, 2.47 to 9.32, 1.27 to 4.00, 0.31 to 3.41, 0.44 to 5.48, 0.47 to 4.19, 1.74 to 13.8, and 0.47 to 2.01 μm, respectively, at an exposure period of at least 48 hrs.

14. The chalcone linked imidazolone compound of formula 3a, 3b, 3f, 4a, 4f, 5a, 5b, 5d, 5f or 12b as claimed in claim 3, exhibiting an in vitro anticancer activity against LOX IMVI, MALME-3M, M14, MDA-MB-435, SK-MEL-2, SK-MEL-28, SK-MEL-5, UACC-257, and UACC-62 melanoma cancer cell lines with $GI_{50}$ in the range of 1.59 to 6.81, 2.03 to 13.3, 1.63 to 8.69, 1.85 to 8.26, 1.53 to 4.07, 0.48 to 2.06, 0.72 to 3.04, 1.23 to 3.02, 1.72 to 18.1, and 0.85 to 4.13 μm, respectively, at an exposure period of at least 48 hrs.

* * * * *